US011708371B2

(12) United States Patent
Chung et al.

(10) Patent No.: US 11,708,371 B2
(45) Date of Patent: Jul. 25, 2023

(54) PROCESS FOR MAKING BETA 3 AGONISTS AND INTERMEDIATES

(71) Applicant: Merck Sharp & Dohme Corp., Rahway, NJ (US)

(72) Inventors: John Y. L. Chung, Edison, NJ (US); Kevin Campos, Berkeley Heights, NJ (US); Edward Cleator, Cambridge (GB); Robert F. Dunn, Towaco, NJ (US); Andrew Gibson, Hoddesdon (GB); R. Scott Hoerrner, Westfield, NJ (US); Stephen Keen, Hoddesdon (GB); Dave Lieberman, Hoddesdon (GB); Zhuqing Liu, Edison, NJ (US); Joseph Lynch, Plainfield, NJ (US); Kevin M. Maloney, Piscataway, NJ (US); Feng Xu, Staten Island, NY (US); Nobuyoshi Yasuda, Mountainside, NJ (US); Naoki Yoshikawa, Hyogo (JP); Yong-Li Zhong, Edison, NJ (US)

(73) Assignee: Merck Sharp & Dohme Corp., Rahway, NJ (US)

(*) Notice: Subject to any disclaimer, the term of this patent is extended or adjusted under 35 U.S.C. 154(b) by 147 days.

(21) Appl. No.: 17/155,982

(22) Filed: Jan. 22, 2021

(65) Prior Publication Data
US 2021/0221815 A1     Jul. 22, 2021

Related U.S. Application Data

(60) Continuation of application No. 16/590,180, filed on Oct. 1, 2019, now Pat. No. 10,899,771, which is a continuation of application No. 16/133,320, filed on Sep. 17, 2018, now Pat. No. 10,435,410, which is a continuation of application No. 15/808,740, filed on Nov. 9, 2017, now Pat. No. 10,087,189, which is a division of application No. 15/057,427, filed on Mar. 1, 2016, now Pat. No. 9,822,121, which is a continuation of application No. 14/354,158, filed as application No. PCT/US2012/061252 on Oct. 22, 2012, now abandoned.

(60) Provisional application No. 61/552,195, filed on Oct. 27, 2011.

(51) Int. Cl.
| | |
|---|---|
| C07D 487/04 | (2006.01) |
| C07D 403/12 | (2006.01) |
| C07D 207/09 | (2006.01) |
| C07D 263/06 | (2006.01) |
| A61K 31/4196 | (2006.01) |
| A61K 31/519 | (2006.01) |

(52) U.S. Cl.
CPC ........ *C07D 487/04* (2013.01); *A61K 31/4196* (2013.01); *A61K 31/519* (2013.01); *C07D 207/09* (2013.01); *C07D 263/06* (2013.01); *C07D 403/12* (2013.01); *C07B 2200/13* (2013.01)

(58) Field of Classification Search
CPC .. C07D 487/04; C07D 207/09; C07D 263/06; C07D 403/12; A61K 31/4196; A61K 31/519; C07B 2200/13; A61P 43/00; A61P 13/10
See application file for complete search history.

(56) References Cited

U.S. PATENT DOCUMENTS

| | | | |
|---|---|---|---|
| 8,247,415 B2 | 8/2012 | Berger et al. | |
| 8,399,480 B2 | 3/2013 | Berger et al. | |
| 8,653,260 B2 | 2/2014 | Berger et al. | |
| 8,748,433 B2 | 6/2014 | Berger et al. | |
| 9,809,536 B2 | 11/2017 | Chung et al. | |
| 9,822,121 B2 * | 11/2017 | Chung | A61P 13/10 |
| 10,087,189 B2 | 10/2018 | Chung et al. | |
| 10,287,289 B2 | 5/2019 | Xu et al. | |
| 10,435,410 B2 | 10/2019 | Chung et al. | |
| 10,577,316 B2 | 3/2020 | Chung et al. | |
| 10,696,681 B2 | 6/2020 | Xu et al. | |
| 10,899,771 B2 | 1/2021 | Chung et al. | |
| 11,124,478 B2 | 9/2021 | Chung et al. | |
| 2002/0028835 A1 | 3/2002 | Hu et al. | |
| 2007/0185136 A1 | 8/2007 | Courtemanche et al. | |
| 2009/0191605 A1 | 7/2009 | Liang et al. | |
| 2009/0253705 A1 | 10/2009 | Berger et al. | |
| 2011/0028481 A1 | 2/2011 | Berger et al. | |
| 2012/0202819 A1 | 8/2012 | Edmondson et al. | |
| 2012/0258963 A1 | 10/2012 | Berger et al. | |
| 2012/0322136 A1 | 12/2012 | Mundorff et al. | |
| 2013/0053403 A1 | 2/2013 | Berger et al. | |
| 2014/0242645 A1 | 8/2014 | Chung et al. | |

(Continued)

FOREIGN PATENT DOCUMENTS

| | | |
|---|---|---|
| WO | WO 03/072572 A1 | 9/2003 |
| WO | WO 2009/124166 A1 | 10/2009 |

(Continued)

OTHER PUBLICATIONS

Haynes et al., Dissociation Constants of Organic Acids and Bases, CRC Handbook of Chemistry and Physics,. 1992, 1-10, 5.
Morriello, "Design of a Novel Pyrrolidine Scaffold Utilized in the Discovery of Potent and Selective Human Beta 3 adrenergic Receptor Agonists," Bioorganic & Medicinal Chemistry Letters, 2011, 1865-1870, 21 (6).
International Search Report of International Appl. No. PCT/US2012/061252 dated Jan. 18, 2013.

(Continued)

*Primary Examiner* — John M Mauro

(57) ABSTRACT

The present invention is directed to processes for preparing beta 3 agonists of Formula (I) and Formula (II) and their intermediates. The beta 3 agonists are useful in the treatment of certain disorders, including overactive bladder, urinary incontinence, and urinary urgency.

13 Claims, 1 Drawing Sheet

(56) References Cited

U.S. PATENT DOCUMENTS

| | | |
|---|---|---|
| 2015/0087832 A1 | 3/2015 | Chung et al. |
| 2016/0176884 A1 | 6/2016 | Chung et al. |
| 2017/0145014 A1 | 5/2017 | Xu et al. |
| 2018/0029981 A1 | 2/2018 | Chung et al. |
| 2020/0290962 A1 | 9/2020 | Chung et al. |
| 2020/0392141 A1 | 12/2020 | Xu et al. |
| 2022/0073459 A1 | 3/2022 | Chung et al. |
| 2022/0073523 A1 | 3/2022 | Xu et al. |

FOREIGN PATENT DOCUMENTS

| | | |
|---|---|---|
| WO | WO 2009/124167 A1 | 10/2009 |
| WO | WO 2011/043942 A1 | 4/2011 |
| WO | WO 2013/062878 A1 | 5/2013 |
| WO | WO 2013/062881 A1 | 5/2013 |
| WO | WO 2013/074650 A1 | 5/2013 |
| WO | WO 2014/150639 A1 | 9/2014 |

OTHER PUBLICATIONS

Wuts et al., The Role of Protective Groups in Organic Synthesis, Greene's Protecting Groups inOrganic Synthesis, 2007, Ch. 1, 1-15, 4th Edition.

CRC Handbook, Dissociation Constants of Organic Acids and Bases, May 25, 1992, pp. 1-10.

Adkins, H. and Billica, H.R., "The Preparation of Raney Nickel Catalysts and their Use Under Conditions Comparable with Those for Platinum and Palladium Catalysts," *Journal of American Chemistry Society* 70(2):695-698, American Chemical Society, United States (1948).

Devos, D. and Valencia, A., "Practical limits of function prediction," *Proteins: Structure, Function, and Genetics* 41:98-107, Wiley-Liss, Inc., United States (2000).

Dong, S., et al., "Convenient syntheses of homopropargylglycine," *Journal of Peptide Science* 14:1148-1150, John Wiley & Sons, Ltd., England (2008).

Huisman, G.W., et al., "Practical chiral alcohol manufacture using ketoreductases," *Current Opinion in Chemical Biology* 14:122-129, Elsevier Ltd., England (2009).

Hultin, P.G., "A Guide to Solvents and Reagents in Introductory Organic Chemistry for students in 2.222," 20 pages (2002).

Kaiser, H-P. and Muchowski, J.M., "Catalytic Hydrogenation of Pyrroles at Atmospheric Pressure," *Journal of Organic Chemistry* 49(2):4203-4209, American Chemical Society, United States (1984).

Kisselev, L., "Polypeptide Release Factors in Prokaryotes and Eukaryotes: Same Function, Different Structure," *Structure* 10(1):8-9, Elsevier Science Ltd., England (2002).

Whisstock, J.C. and Lesk, A.M., "Prediction of protein function from protein sequence and structure," *Quarterly Reviews of Biophysics* 36(3):307-340, Cambridge University Press, United Kingdom (2003).

Witkowski, A., et al., "Conversion of a β-Ketoacyl Synthase to a Malonyl Decarboxylase by Replacement of the Active-Site Cysteine with Glutamine," *Biochemistry* 38(36):11643-11650, American Chemical Society, United States (1999).

Xu, F., et al., "Asymmetric Synthesis of cis-2,5-Disubstituted Pyrrolidine, the Core Scaffold of $\beta_3$-AR Agonists," *Organic Letters* 15(6):1342-1345, American Chemical Society, United States (2013).

International Preliminary Report on Patentability and Written Opinion for International Application No. PCT/US2009/039249, The International Bureau of WIPO, Geneva, Switzerland, dated Oct. 5, 2010, 6 pages.

International Preliminary Report on Patentability and Written Opinion for International Application No. PCT/US2009/039253 The International Bureau of WIPO, Geneva, Switzerland, dated Oct. 5, 2010, 5 pages.

International Preliminary Report on Patentability and Written Opinion for International Application No. PCT/US2014/023858, The International Bureau of WIPO, Geneva, Switzerland, dated Sep. 15, 2015, 5 pages.

International Preliminary Report on Patentability and Written Opinion for International Application No. PCT/US2012/061252, The International Bureau of WIPO, Geneva, Switzerland, dated Apr. 29, 2014, 4 pages.

International Preliminary Report on Patentability and Written Opinion for International Application No. PCT/US2012/061249, The International Bureau of WIPO, Geneva, Switzerland, dated Apr. 29, 2014, 4 pages.

International Search Report for International Application No. PCT/US2009/039249, European Patent Office, Netherlands, dated Aug. 31, 2009, 4 pages.

International Search Report for International Application No. PCT/US2009/039253, European Patent Office, Netherlands, dated Jun. 17, 2009, 3 pages.

International Search Report for International Application No. PCT/US2014/023858, European Patent Office, Netherlands, dated Jun. 6, 2014, 3 pages.

International Search Report for International Application No. PCT/US2012/061249, European Patent Office, Netherlands, dated Jun. 6, 2014, 3 pages.

Extended European Search Report for EP Application No. 12842776.2, Munich, Germany, dated Mar. 12, 2015, 4 pages.

Office Action dated Aug. 17, 2017, in U.S. Appl. No. 14/776,366, Xu, F. et al., § 371(c) date Sep. 14, 2015, 15 pages.

Extended European Search Report dated Dec. 18, 2019, in European Patent Application 19184972.8, Inventors Xu F. et al.

Ebenezer, W.J. and Wight, P., "Ketones: a,i3-Unsaturated Ketones," in *Comprehensive Organic Functional Group Transformations*, vol. 3, Katritzky, A.R., et al., eds., pp. 205-276, Elsevier Ltd., England (1995).

Extended European Search Report for EP Application No. 14768236.3, Munich, Germany, dated Nov. 28, 2016, 7 pages.

Koszelewski, D., et at., "Immobilization of w-transaminases by encapsulation in a solgel/ celite matrix," *Journal of Molecular Catalysis B: Enzymatic* 63:39-44, Elsevier B.V., Netherlands (2010).

Martin, A.R., et al., "Characterization of Free and Immobilized ($)-aminotransferase for Acetophenone Production," *Applied Microbiology and Biotechnology* 76(4):843-851, Springer International, Germany (2007).

Mateo, C., et al., "Epoxy Sepabeads: A Novel Epoxy Support for Stabilization of Industrial Enzymes via Very Intense Multipoint Covalent Attachment," *Biotechnology Progress* 18(3):629-634, American Chemical Society and American Institute of Chemical Engineers, United States (2002).

North, M., "Nitriles: General Methods and Aliphatic Nitriles," in *Comprehensive Organic Functional Group Transformations*, vol. 3, Katritzky, A.R., et al., eds., pp. 611-640, Elsevier Ltd., England (1995).

Parkes, K.E.B. and Richardson, S.K., "Ketones: Dialkyl Ketones," in *Comprehensive Organic Functional Group Transformations*, vol. 3, Katritzky, A.R., et at., eds., pp. 111-204, Elsevier Ltd., England (1995).

Sonogashira, K., "Palladium-Catalyzed Alkynylation: Sonogashira Alkyne Synthesis," in Handbook of Organopal/adium *Chemistry for Organic Synthesis*, Negishi, E-1., ed., pp. 493-529, John Wiley & Sons, Inc., United States (2002).

Iruppo, M.D. and Hughes, G., "Development of an Improved Immobilized CAL-B for the Enzymatic Resolution of a Key Intermediate to Odanacatib," *Organic Process Research & Development* 15(5):1033-1035, American Chemical Society, United States (2011).

Yi, S.S., et al., "Covalent Immobilization of w-transaminase from Vibrio fluvia/is JS17 on chitosan beads," *Process Biochemistry* 42(5):895-898, Elsevier Ltd., England (2007).

Office Action dated Jun. 2, 2020, in U.S. Appl. No. 16/590,180 Chung, John Y.L.. et al., filed Oct. 1, 2019, 8 pages.

Office Action dated Aug. 18, 2022 in U.S. Appl. No. 17/399,274 Xu, Feng, et al., filed Aug. 11, 2021, 6 pages.

\* cited by examiner

FIGURE 1. XRPD Pattern of the Crystalline Anhydrous form of Compound i-11 of Example 1.
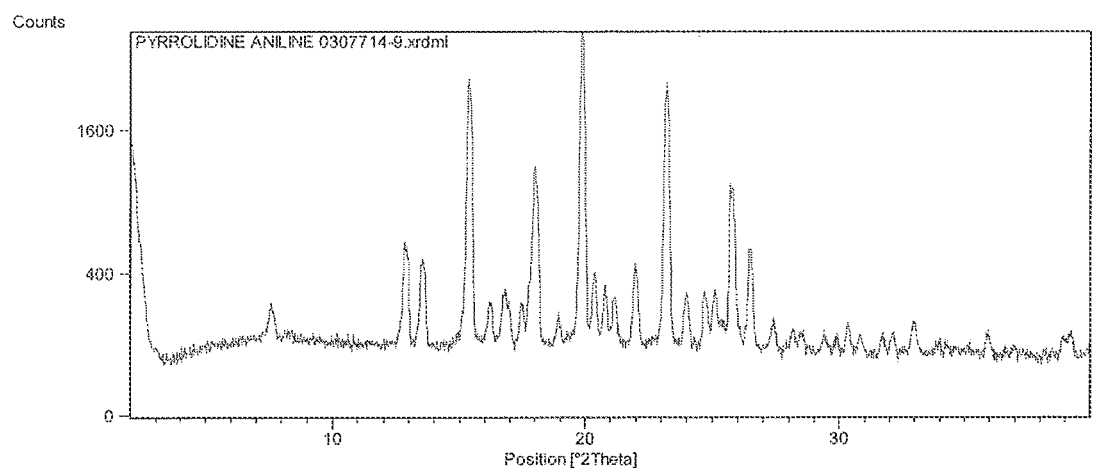
FIGURE 2. XRPD Pattern of the Crystalline Hemihydrate form of Compound i-11 of Example 1.
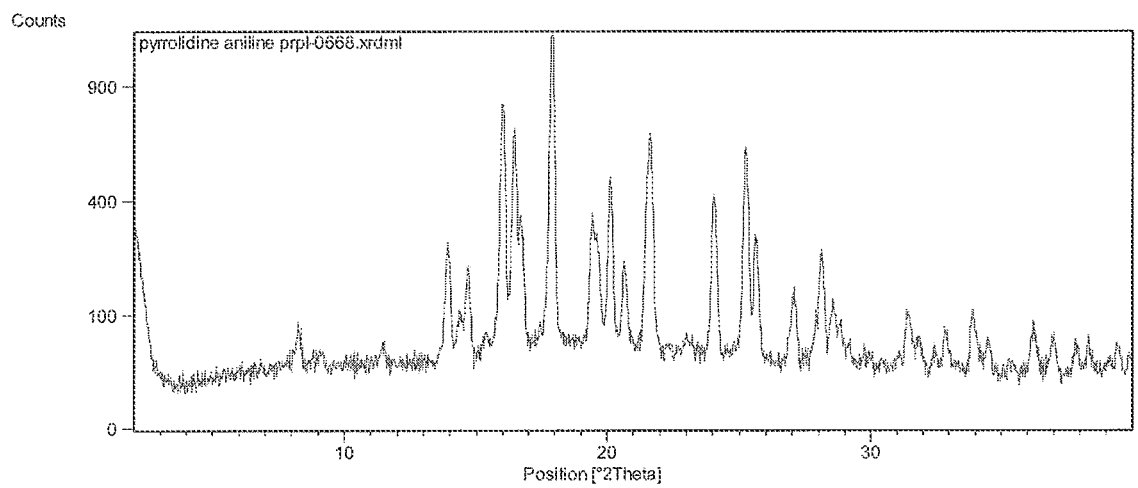

PROCESS FOR MAKING BETA 3 AGONISTS AND INTERMEDIATES

CROSS-REFERENCE TO RELATED APPLICATIONS

This is a continuation application of U.S. application Ser. No. 16/590,180, filed on Oct. 1, 2019, which is a continuation of U.S. application Ser. No. 16/133,320, filed on Sep. 17, 2018, which is a continuation of U.S. application Ser. No. 15/808,740, filed on Nov. 9, 2017, which is a divisional application of U.S. application Ser. No. 15/057,427, filed on Mar. 1, 2016, which is a continuation application of U.S. application Ser. No. 14/354,158, filed on Apr. 25, 2014, which is a 371 National Stage Application of PCT/US12/61252, filed on Oct. 22, 2012, which claims priority from U.S. Provisional Application No. 61/552,195, filed on Oct. 27, 2011. Each of these applications is incorporated herein by reference in its entirety.

BACKGROUND OF THE INVENTION

This application is directed to synthetic processes for making beta 3 agonists of Formula (I) and Formula (II) and their intermediate compounds.

Beta Adrenergic receptors (βAR) are present in detrusor smooth muscle of various species, including human, rat, guinea pig, rabbit, ferret, dog, cat, pig and non-human primate. However, pharmacological studies indicate there are marked species differences in the receptor subtypes mediating relaxation of the isolated detrusor; β1AR predominate in cats and guinea pig, β2AR predominate in rabbit, and β3AR contribute or predominate in dog, rat, ferret, pig, cynomolgus and human detrusor. Expression of βAR subtypes in the human and rat detrusor has been examined by a variety of techniques, and the presence of β3AR was confirmed using in situ hybridization and/or reverse transcription-polymerase chain reaction (RT-PCR). Real time quantitative PCR analyses of β1AR, β2AR and β3AR mRNAs in bladder tissue from patients undergoing radical cystectomy revealed a preponderance of β3AR mRNA (97%, cf 1.5% for β1AR mRNA and 1.4% for β2AR mRNA). Moreover, β3AR mRNA expression was equivalent in control and obstructed human bladders. These data suggest that bladder outlet obstruction does not result in downregulation of β3AR, or in alteration of β3AR-mediated detrusor relaxation. β3AR responsiveness also has been compared in bladder strips obtained during cystectomy or enterocystoplasty from patients judged to have normal bladder function, and from patients with detrusor hyporeflexia or hyperreflexia. No differences in the extent or potency of β3AR agonist mediated relaxation were observed, consistent with the concept that the β3AR activation is an effective way of relaxing the detrusor in normal and pathogenic states. Functional evidence in support of an important role for the β3AR in urine storage emanates from studies in vivo. Following intravenous administration to rats, the rodent selective β3AR agonist CL316243 reduces bladder pressure and in cystomeric studies increases bladder capacity leading to prolongation of micturition interval without increasing residual urine volume.

Overactive bladder (OAB) is characterized by the symptoms of urinary urgency, with or without urgency urinary incontinence, usually associated with frequency and nocturia. The prevalence of OAB in the United States and Europe has been estimated at 16 to 17% in both women and men over the age of 18 years. Overactive bladder is most often classified as idiopathic, but can also be secondary to neurological condition, bladder outlet obstruction, and other causes. From a pathophysiologic perspective, the overactive bladder symptom complex, especially when associated with urge incontinence, is suggestive of detrusor overactivity. Urgency with or without incontinence has been shown to negatively impact both social and medical well-being, and represents a significant burden in terms of annual direct and indirect healthcare expenditures. Importantly, current medical therapy for urgency (with or without incontinence) is suboptimal, as many patients either do not demonstrate an adequate response to current treatments, and/or are unable to tolerate current treatments (for example, dry mouth associated with anticholinergic therapy).

The present invention describes efficient and economical processes as described in more detail below for the preparation of the beta 3 agonists of Formula (I) and Formula (II) and intermediate compounds that can be used for making these agonists.

BRIEF DESCRIPTION OF THE DRAWINGS

FIG. 1 (FIG. 1) is a powder X-ray diffraction pattern of the crystalline anhydrous form of compound i-11 of Example 1.

FIG. 2 (FIG. 2) is a powder X-ray diffraction pattern of the crystalline hemihydrate form of compound i-11 of Example 1.

SUMMARY OF THE INVENTION

The present invention is directed to synthetic processes for making beta 3 agonists of Formula (I) and Formula (II) and their intermediate compounds I-11 and I-12.

DESCRIPTION OF THE INVENTION

Described herein is a process of making compound I-11 from compound I-5b through multiple step reactions:

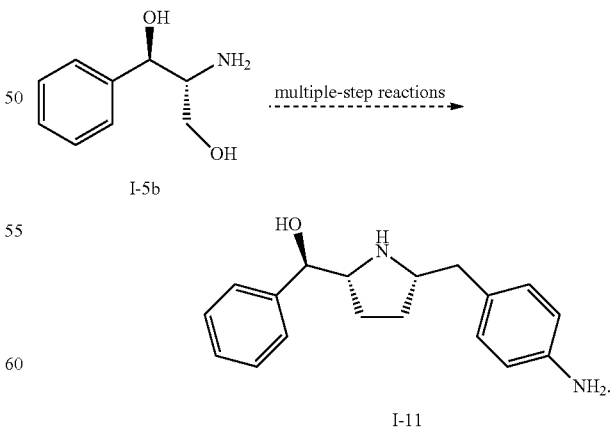

In one embodiment, the multiple-step reactions from compound I-5b to compound I-11 comprise reacting compound I-5b with acetone and $P^1{}_2O$ to produce compound I-6:

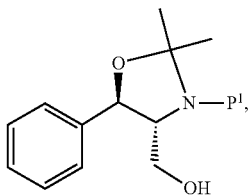

I-6 wherein $P^1$ is selected from the group consisting of Ac, Bn, Boc, Bz, Cbz, DMPM, FMOC, Ns, Moz, and Ts. In one embodiment, $P^1$ is Boc.

In one embodiment, the multiple-step reactions from compound I-5b to compound I-11 comprise oxidizing compound I-6 with an oxidizing agent in the presence of a catalyst to produce compound I-7:

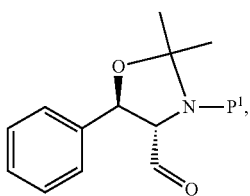

I-7 wherein $P^1$ is selected from the group consisting of Ac, Bn, Boc, Bz, Cbz, DMPM, FMOC, Ns, Moz, and Ts. In one embodiment, $P^1$ is Boc.

Suitable oxidizing agents include, but are not limited to, NaOCl, NaClO$_2$, hydrogen peroxide, Swern oxidation and variants such as pyridine sulfur trioxide, PCC, and DCC. In one embodiment, the oxidizing agent is NaOCl.

The amount of the oxidizing agent is typically 1.1 equiv. to 1.3 equiv., or more specifically, 1.2 equiv. to 1.25 equiv. In one embodiment, the amount of the oxidizing agent is 1.25 equiv.

Suitable catalysts for the above oxidation reaction include, but are not limited to, TEMPO and TEMPO analogues. In one embodiment, the catalyst is TEMPO.

One advantage of the presently described process is that compound I-7 from the oxidation step can be used directly in the next Horner Wadsworth Emmons (hereinafter, "HWE") step to make compound I-8. This one pot process eliminates the need for solvent switch and can increase the yield and reduce cost.

In one embodiment, the oxidation step from I-6 to I-7 can be carried out in the presence of a solvent. Suitable solvents include, but are not limited to, THF, MTBE, CH$_2$Cl$_2$, MeCN, toluene and mixtures thereof. In one embodiment, the solvent is a mixture of toluene and MeCN. In another embodiment, the solvent is a mixture of CH$_2$Cl$_2$ and MeCN.

In one embodiment, the multiple-step reactions from compound I-5b to compound I-11 comprise reacting compound I-7 with phosphate compound A-4:

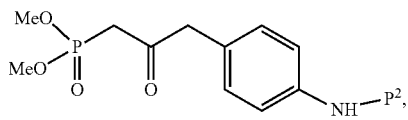

A-4 in the presence of a solvent to produce compound I-8 ("HWE reaction"):

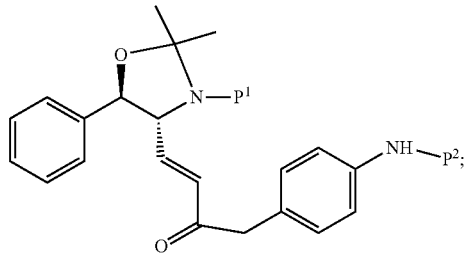

I-8 wherein $P^1$ and $P^2$ are each independently selected from the group consisting of Ac, Bn, Boc, Bz, Cbz, DMPM, FMOC, Ns, Moz, and Ts. In one embodiment, both $P^1$ and $P^2$ are Boc.

Suitable solvents include, but are not limited to, THF, MTBE, CH$_2$Cl$_2$, MeCN, toluene and a mixture comprising two of the foregoing solvents. In one embodiment, the solvent is the mixture of toluene and MeCN.

The HWE reaction is typically carried out at a temperature of −10 to 50° C., or more specifically, 0 to 40° C. In one embodiment, the temperature is 0 to 25° C. In another embodiment, the temperature is 40° C.

The HWE reaction is typically carried out in the presence of a base or a salt. In one embodiment, the base is a tertiary amine. In another embodiment, the base is N,N-diisopropylethylamine (DIPEA).

In one embodiment, the salt is lithium halide, or more specifically, LiCl or LiBr.

In the HWE reaction, an impurity compound I-21 (aldol dimer by-product) may be formed in addition to compound I-8:

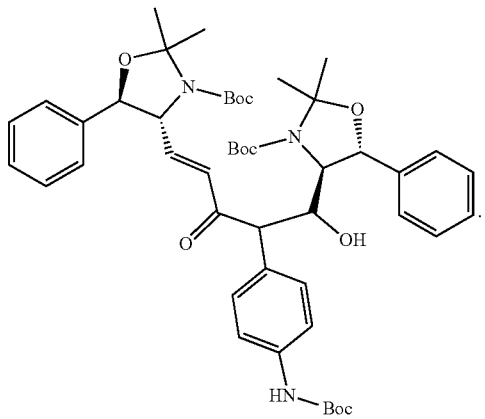

I-21

It has been found that by adjusting pH to between 6.5 and 7.0 after the reaction, higher purity compound I-8 can be obtained with improved yield. Additionally, addition of more reactant compound A-4 has been shown to drive the impurity I-21 to product I-8. In one embodiment, addition of an extra 0.2 equiv. of A-4 can reduce the level of I-21 to from 8 LCAP to 2 LCAP.

Increasing the reaction temperature can speed up the conversion to the desired product compound I-8 and reduce the level of the byproduct compound I-21.

By changing the reaction from a batch process to an addition controlled process, the yield of compound I-8 can be improved and the level of byproduct compound I-21 can be reduced. For example, by adding reactant compound I-7 to a solution containing reactant compound A-4, the level of I-21 can be decreased and the yield of compound I-8 improved.

In one embodiment, a solution containing 1.2 equiv of A-4, 3 equiv. of DIPEA and 3 equiv. of LiCl in 5 volumes of MeCN was prepared and warmed to 40° C. A toluene stream of compound I-7 was then added to this mixture over 3 h, after an additional 30 min aging conversion to product was complete. The level of impurity I-21 was about ~1 LCAP. Sampling the reaction at 1 h intervals showed there was no build-up of compound I-7 in the reaction mixture. After work up the product was isolated with a 90% isolated yield.

It has also been found that using slightly smaller amount of reactant A-4 does not negatively affect the yield of compound I-8. In one embodiment, 1.0 instead of 1.2 equiv. of compound A-4 was used and high yield was still obtained.

Compound A-4 used in the HWE reaction can be prepared from compound A-1:

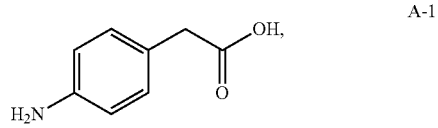 [SMILES: Nc1ccc(CC(=O)O)cc1]
A-1 using similar synthetic steps and conditions as described in A General Procedure for the Preparation of β-Ketophosphonates, Maloney et. al., J. Org. Chem., 74, page 7574-7576 (2009).

In one embodiment, the reduction of compound I-8 to produce compound I-9 is carried out in the presence of a catalyst:

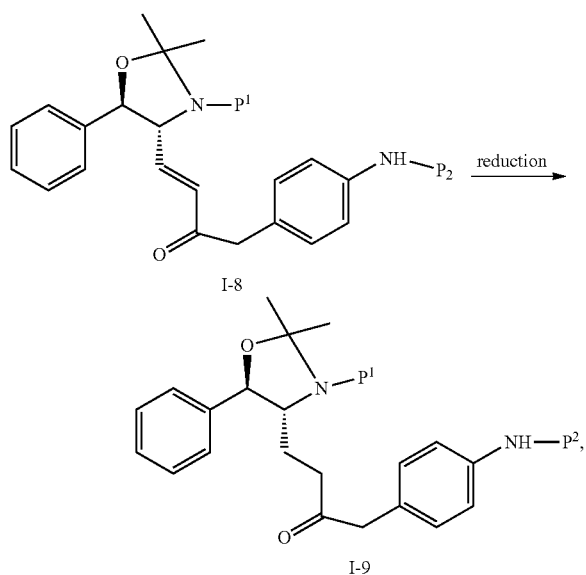

wherein $P^1$ and $P^2$ are each independently selected from the group consisting of Ac, Bn, Boc, Bz, Cbz, DMPM, FMOC, Ns, Moz, and Ts. In one embodiment, both $P^1$ and $P^2$ are Boc.

Suitable catalysts include, but are not limited to, Pd, Raney Ni, Pt, $PdCl_2$, and $Pd(OH)_2$. In one embodiment, the catalyst is 5% Pd/C.

In another embodiment, the reduction from I-8 to I-9 is carried out in the presence of a solvent. Suitable solvents include, but are not limited to, THF, MTBE, $CH_2Cl_2$, MeCN, toluene, methanol, ethanol, 2-propanol and mixtures thereof. In one embodiment, the solvent is THF.

In another embodiment, the reduction reaction is carried out using hydrogen gas at a pressure of 2 to 300 psig, preferably about 40 psig, in the presence of a catalyst.

In one embodiment, compound I-9 reacts with an acid to produce compound I-10 through a cyclization reaction:

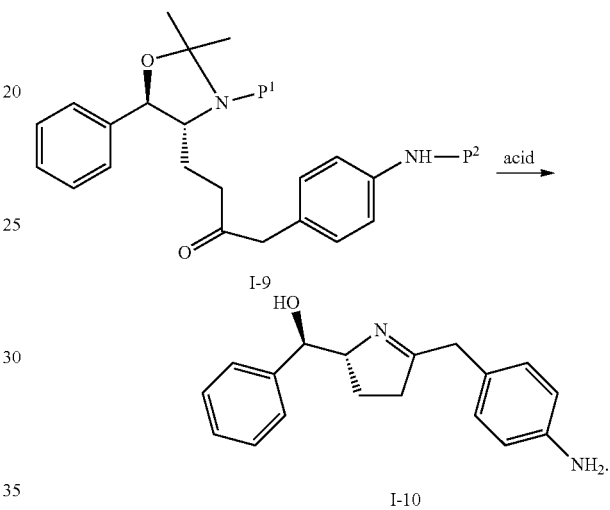

Suitable acids include, but are not limited to, HCl, HBr, TFA, $MeSO_3H$, TfOH, $H_2SO_4$, para-toluenesulfonic acid, and other sulfone acids such as $RSO_3H$ wherein R is $C_{1-6}$alkyl, aryl or substituted aryl. In one embodiment, the acid is HCl.

In one embodiment, HCl is used as acid and an HCl salt of compound I-10 is obtained. In one embodiment, the HCl salt is in the form of bis-HCl salt. In another embodiment, the bis-HCl salt is in the form of a mono-hydrate. In another embodiment, the mono-hydrate of the bis-HCl salt of compound I-10 is a crystalline material.

The conversion from I-9 to I-10 can be carried out at a temperature of 0 to 40° C., or more specifically, 15 to 25° C., or even more specifically, 20 to 25° C. In one embodiment, the temperature is 20 to 25° C.

In one embodiment, compound I-10 is reduced to compound I-11 in the presence of a catalyst:

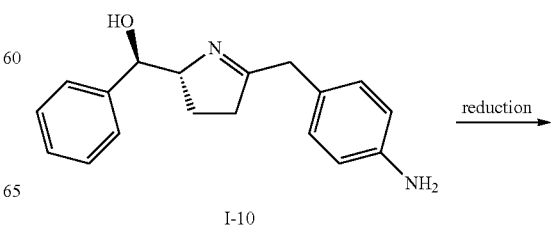

-continued

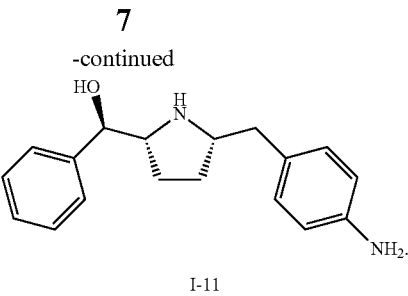

I-11

The reaction conditions for the conversion from I-10 to I-11 can be controlled so a cis-selective hydrogenation process is obtained. In one embodiment, the cis-selective hydrogenation is carried out in the presence of a catalyst. Suitable catalysts include, but are not limited to Pt on alumina, Pd on alumina, Pd/C, Pd(OH)₂—C, Raney Ni, Rh/C, Rh/Al, Pt/C, Ru/C and PtO₂. In one embodiment, the catalyst is Pt on alumina.

In another embodiment, the cis-selective hydrogenation from I-10 to I-11 is carried out in the presence of HMDS, which can protect the hydroxy group in situ and therefore improve the diastereo selectivity. Other suitable protecting reagents include, but are not limited to, TMSCl, TESCl, and TBDMSCl.

In one embodiment, compound I-11 is obtained in the form of a crystalline anhydrous free base. In another embodiment, compound I-11 is obtained in the form of a crystalline free base hemihydrate.

In one embodiment, a process of making compound I-11 comprises:

(a) reducing compound I-8:

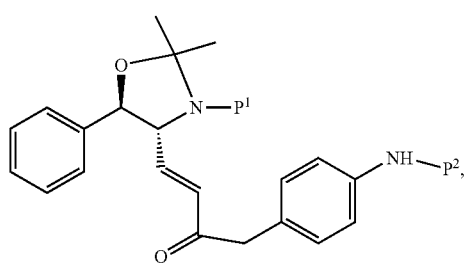

in the presence of a catalyst to produce compound I-9:

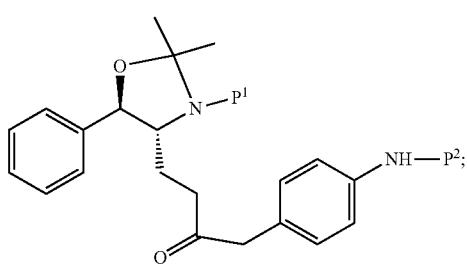

(b) reacting compound I-9 with an acid to produce compound I-10:

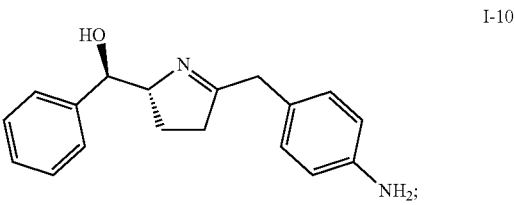 [SMILES: Nc1ccc(CC2=N[C@@H]([C@H](O)c3ccccc3)CC2)cc1]

and (c) reducing compound I-10 in the presence of a catalyst to produce compound I-11:

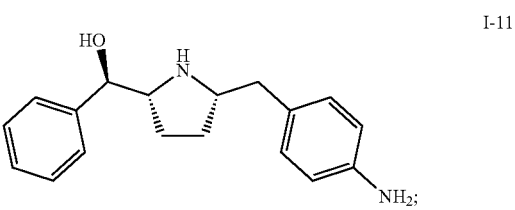

wherein P¹ and P² are each independently selected from the group consisting of Ac, Bn, Boc, Bz, Cbz, DMPM, FMOC, Ns, Moz, and Ts.

In one embodiment, the catalyst in step (a) above is selected from the group consisting of Pd, Raney Ni, Pt, PdCl₂, and Pd(OH)₂.

In one embodiment, the acid in step (b) above is selected from the group consisting of HCl, HBr, TFA, MeSO₃H, TfOH, H₂SO₄, para-toluenesulfonic acid, and RSO₃H wherein R is alkyl, aryl or substituted aryl.

In one embodiment, the reduction of step (c) is carried out in the presence of HMDS and the catalyst used is selected from the group consisting of Pt on alumina, Pd on alumina, Pd/C, Pd(OH)₂—C, Raney Ni, Rh/C, Rh/Al, Pt/C, Ru/C and PtO₂.

In one embodiment, a process of making compound I-11 comprises:

(a) reacting compound I-7:

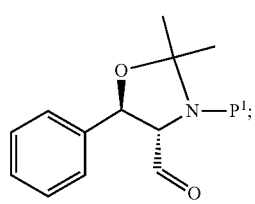

with phosphate compound A-4:

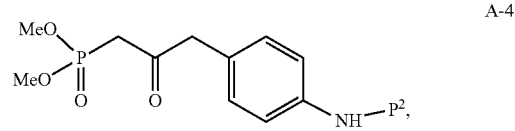

to produce compound I-8:

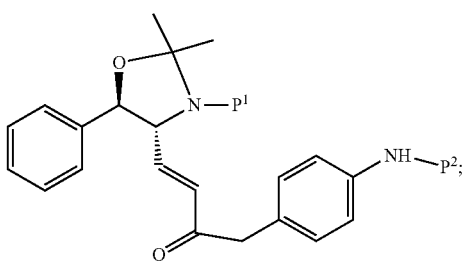

I-8 wherein the reaction is carried out at a temperature of about 20 to 40° C. and in the presence of a solvent selected from the group consisting of THF, MTBE, CH$_2$Cl$_2$, MeCN, toluene and a mixture comprising two of the foregoing solvents;

(b) reducing compound I-8 in the presence of a catalyst selected from the group consisting of Pd, Raney Ni, Pt, PdCl$_2$, and Pd(OH)$_2$ to produce compound I-9:

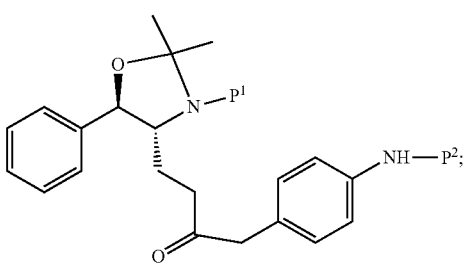

I-9

(c) reacting compound I-9 with an acid to produce compound I-10:

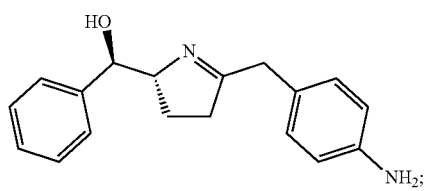

I-10 and (d) reducing compound I-10 in the presence of a catalyst to produce compound I-11:

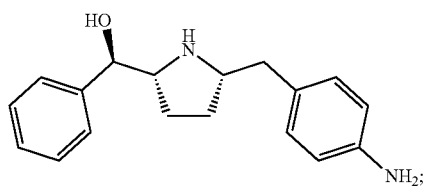

I-11 wherein P$^1$ and P$^2$ are each independently selected from the group consisting of Ac, Bn, Boc, Bz, Cbz, DMPM, FMOC, Ns, Moz, and Ts.

In another embodiment, a process of making compound I-11 comprises:

(a) reacting compound I-5b:

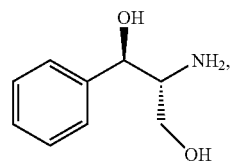

I-5b with acetone and Boc$_2$O to produce compound I-6:

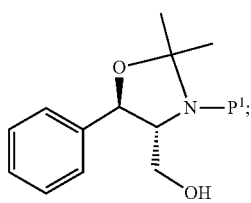

I-6

(b) oxidizing compound I-6 with an oxidizing agent in the presence of a solvent and a catalyst to produce compound I-7:

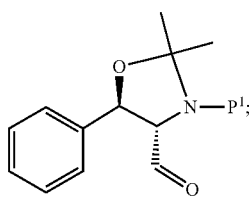

I-7

(c) reacting compound I-7 with phosphate compound A-4:

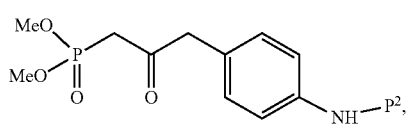

A-4 to produce compound I-8:

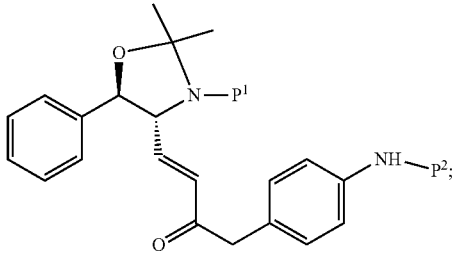

I-8 wherein the reaction is carried out at a temperature of about 20 to 40° C. and in the presence of a solvent selected from the group consisting of THF, MTBE, CH$_2$Cl$_2$, MeCN, toluene and a mixture comprising two of the foregoing solvents;

(d) reducing compound I-8 in the presence of a catalyst selected from the group consisting of Pd, Raney Ni, Pt, PdCl$_2$, and Pd(OH)$_2$ to produce compound I-9:

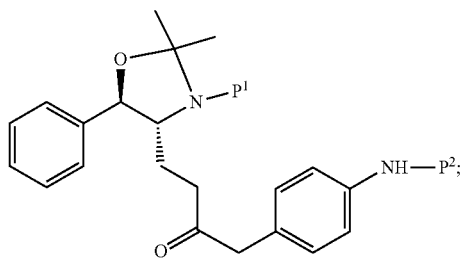

I-9

(e) reacting compound I-9 with an acid to produce compound I-10:

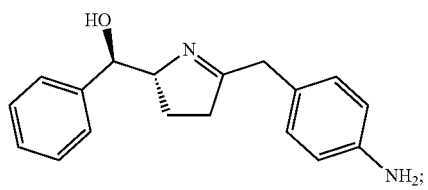

I-10 and (f) reducing compound I-10 in the presence of a catalyst to produce compound I-11:

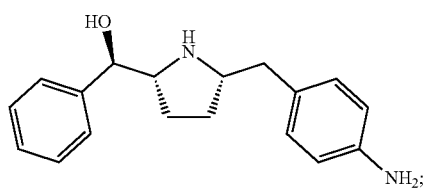

I-11 wherein P$^1$ is Boc and P$^2$ is selected from the group consisting of Ac, Bn, Boc, Bz, Cbz, DMPM, FMOC, Ns, Moz, and Ts.

Compound I-11 can be used as an intermediate compound for making compounds of Formula (I) or Formula (II):

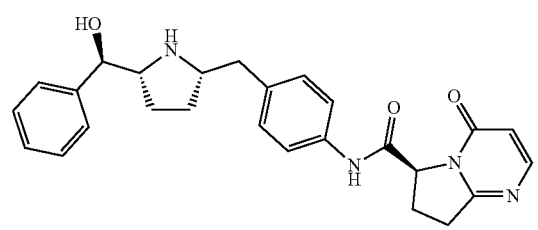

(I)

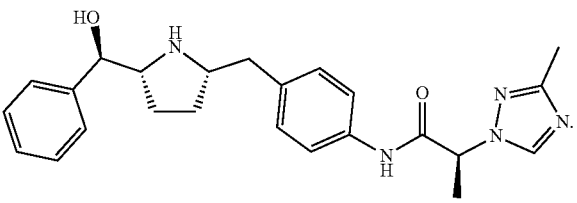

(II)

Also described herein is a process of making compound I-12:

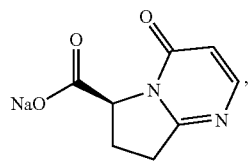

I-12 comprising reacting compound I-14:

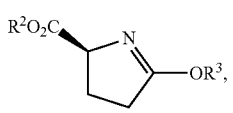

I-14 with compound I-15:

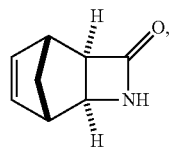

I-15 wherein R$^2$ and R$^3$ are each independently selected from the group consisting of C$_{1-6}$alkyl, benzyl, and phenyl. In one embodiment, R$^2$ and R$^3$ are each independently selected from the group consisting of methyl, ethyl, propyl, butyl and benzyl. In another embodiment, R$^2$ and R$^3$ are both methyl.

In one embodiment, the above process for making compound I-12 comprises 2 steps:

(a) reacting compound I-14 with compound I-15 to produce compound i-17:

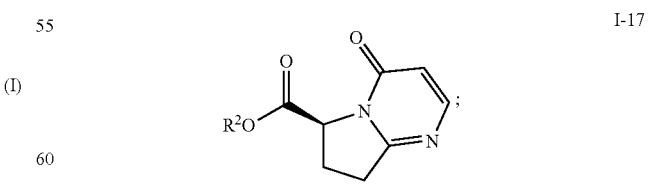

I-17 and (b) hydrolyzing compound I-17 to produce compound I-12.

The above step (a) can be carried out in the presence of a solvent. Suitable solvents include, but are not limited to, ethyl benzene, toluene, trifluorotoluene, xylenes, cumene, and tert-butyl benzene. In one embodiment, the solvent is ethyl benzene.

The above step (a) can be carried out at a temperature of 110° C. to 150° C., or more specifically, 125° C. to 135° C. In one embodiment, the temperature is 125° C. to 135° C.

The above hydrolysis step (b) can be carried out in the presence of a base. Suitable bases include, but are not limited to, NaOH, LiOH, KOH, CsOH, Ca(OH)$_2$, Ba(OH)$_2$, Mg(OH)$_2$, K$_2$CO$_3$, Na$_2$CO$_3$, and Cs$_2$CO$_3$. In one embodiment, the base is NaOH.

The above step (b) can be carried out in the presence of a solvent. Suitable solvents include, but are not limited to, methanol, water, THF, EtOH, IPA, α-methyl-THF, and mixtures thereof. In one embodiment, the solvent is the mixture of methanol/water, THF/water, EtOH/water, IPA/water, or α-methyl-THF/water. In another embodiment, the solvent is a mixture of methanol/water.

In one embodiment, compound I-14 can be prepared from reacting compound I-13:

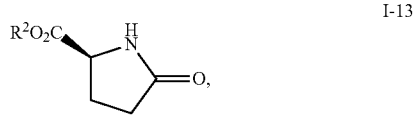

I-13 with (MeO)$_2$SO$_2$, wherein R$^2$ is as defined above.

In one embodiment, R$^2$ is selected from the group consisting of methyl, ethyl, propyl, butyl and phenyl. In another embodiment, R$^2$ is methyl.

In one embodiment, the above step from compound I-13 to compound I-14 is carried out without a solvent.

In another embodiment, the above step from compound I-13 to compound I-14 is carried out at a temperature of 10° C. to 85° C., or more specifically, 25° C. to 65° C. In one embodiment, the temperature is 25° C. to 65° C.

Further described herein is a process of making a compound of Formula (I):

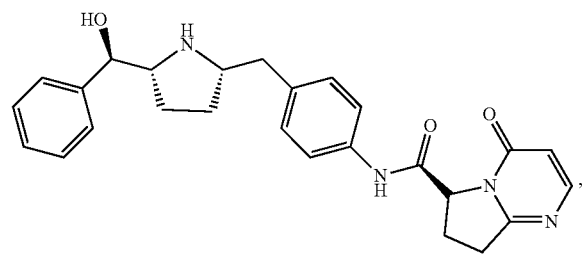

(I)

comprising reacting compound I-11 with compound I-12.

The reaction between I-11 and I-12 can be carried out in the presence of a coupling reagent. Suitable coupling reagents include, but are not limited to, CDI, DCC, EDC, EDC methiodide, T3P, HATU, HBTU and mix-anhydrides. In one embodiment, the coupling reagent is EDC.

The reaction between I-11 and I-12 can be carried out in the presence of a solvent while the substrate is treated with an acid such as HCl, MeSO$_3$H, H$_2$SO$_4$ to selectively protect the secondary pyrrolidine amine. Suitable solvents include, but are not limited to, both aqueous and non-aqueous solvents such as MeOH, EtOH, IPA, n-PrOH, MeCN, DMF, DMAc, THF, EtOAc, IPAc, or toluene.

A promoter can be used in the reaction between I-11 and I-12. Suitable promotors include, but are not limited to, HOBT and HOPO.

Suitable pH values for the reaction between I-11 and I-12 can be 2.5 to 5.0, or more specifically, 3.0 to 4.0, or even more specifically, 3.0 to 3.5. The pH can be adjusted to the desired ranges using an acid such as HCl, HBr, HI, HNO$_3$, H$_2$SO$_4$, H$_3$PO$_4$, TFA and MeSO$_3$H. In one embodiment, the pH is 3.0 to 3.5. In another embodiment, the pH is 3.3 to 3.5.

Also described herein is a process of making a compound of Formula (II):

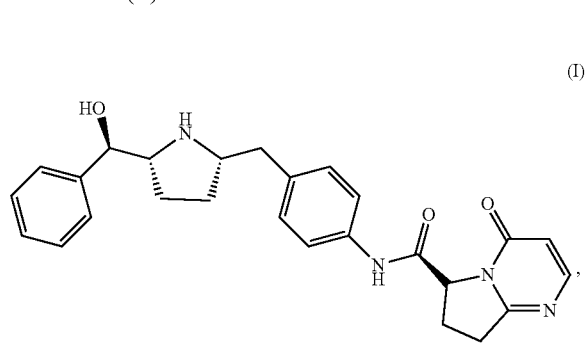

(I)

comprising reacting compound I-11 with a suitable salt of compound I-30:

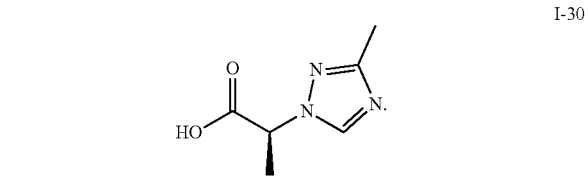

I-30

In one embodiment, the salt of compound I-30 is the lithium salt.

In one embodiment, the reaction between I-11 and I-30 is carried out in the presence of an acid. In one embodiment, the solvent is selected from the group consisting of HCl, HBr, HI, HNO$_3$, H$_2$SO$_4$, H$_3$PO$_4$, TFA and MeSO$_3$H.

In one embodiment, the reaction between I-11 and I-30 is carried out in the presence of a solvent. In one embodiment, the solvent is selected from the group consisting of MeOH, EtOH, IPA, n-PrOH, MeCN, DMF, DMAc, THF, EtOAc, IPAc, or toluene.

The lithium salt of compound I-30 can be prepared from ethyl pyruvate (compound i-37) through multiple step reactions as illustrated in Scheme 4 and Example 4:

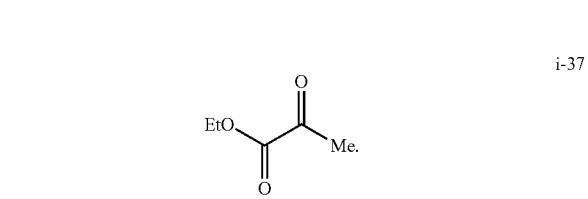

i-37

As used herein, the term "alkyl" means both branched- and straight-chain saturated aliphatic hydrocarbon groups having the specified number of carbon atoms. For example, $C_{1-6}$alkyl includes, but is not limited to, methyl (Me), ethyl (Et), n-propyl (Pr), n-butyl (Bu), n-pentyl, n-hexyl, and the isomers thereof such as isopropyl (i-Pr), isobutyl (i-Bu), secbutyl (s-Bu), tert-butyl (t-Bu), isopentyl, sec-pentyl, tert-pentyl and isohexyl.

As used herein, the term "aryl" refers to an aromatic carbocycle. For example, aryl includes, but is not limited to, phenyl and naphthale.

Throughout the application, the following terms have the indicated meanings unless noted otherwise:

| Term | Meaning |
|---|---|
| Ac | Acyl (CH$_3$C(O)—) |
| Aq | Aqueous |
| Bn | Benzyl |
| BOC (Boc) | t-Butyloxy carbonyl |
| BOC$_2$O | Di-tert-butyl dicarbonate |
| Bz | Benzoyl |
| ° C. | Degree Celsius |
| Calc. or calc'd | Calculated |
| Cbz | Carbobenzyloxy |
| CDI | 1,1'Carbonyldiimidazole |
| DCC | N,N'-Dicyclohexycarbodiimide |
| DCM | Dichloromethane |
| DKR | Dynamic kinetic resolution |
| DMAc | N,N-dimethylacetamide |
| DMAP | 4-Dimethylaminopyridine |
| DMF | N,N-dimethylformamide |
| DMPM | 3,4-Dimethoxybenzyl |
| DMSO | Dimethyl sulfoxide |
| EDC | 1-Ethyl-3-(3-dimethylaminopropyl) carbodiimide |
| Eq. or equiv. | Equivalent(s) |
| ES-MS and ESI-MS | Electron spray ion-mass spectroscopy |
| Et | Ethyl |
| EtOAc | Ethyl acetate |
| FMOC | 9-Fluorenylmethyloxy carbonyl |
| g | Gram(s) |
| h or hr | Hour(s) |
| HATU | O-(7-Azabenzotriazol-1-yl)-N,N',N'-tetramethyluronium hexafluorophosphate |
| HBTU | O-(Benzotriazol-1-yl)-N,N,N',N'-tetramethyluronium hexafluorophosphate) |
| HCl | Hydrogen chloride |
| HMDS | Hexamethyldisilazane |
| HPLC | High performance liquid chromatography |
| HOAc | Acetic acid |
| HOBT | 1-Hydroxy-1H-benzotriazole |
| HOPO | 2-Hydroxypyridine-A-oxide |
| IPA | Isopropyl alcohol |

| Term | Meaning |
|---|---|
| kg | Kilogram(s) |
| LC/MS or LC-MASS | Liquid chromatography mass spectrum |
| L | Liter(s) |
| LAH or LiAlH$_4$ | Lithium aluminium hydride |
| LCAP | Liquid Chromatography Area Percent |
| LiBH$_4$ | Lithium borohydride |
| M | Molar(s) |
| Me | Methyl |
| MeCN | Acetonitrile |
| MeOH | Methanol |
| min | Minute(s) |
| mg | Milligram(s) |
| mL | Milliliter(s) |
| mmol | Millimole(s) |
| Moz or MeOZ | p-Methoxybenzyl carbonyl |
| MTBE | Methyl tert-butyl ether |
| NADP | Nicotinamide adenine dinucleotide phosphate sodium salt |
| nM | Nanomolar |
| Ns | 4-Nitrobenzene sulfonyl |
| PCC | Pyridinium chlorochromate |
| 5% Pd/C | Palladium, 5 weight percent on activated carbon |
| Ph | Phenyl |
| r.t. or rt or RT | RT |
| Sat. | Saturated |
| TBDMSCl | Tert-Butyldimethylsilyl chloride |
| TEA or Et$_3$N | Triethylamine |
| TEMPO | 1-Oxyl-2,2,6,6-tetramethylpiperidine |
| TESCl | Triethylchlorosilane |
| TFA | Trifluoroacetic acid |
| THF | Tetrahydrofuran |
| TMSCl | Trimethylchlorosilane |
| Ts | p-Toluene sulfonyl |

Reaction Schemes below illustrate the synthetic steps, reagents and conditions employed in the synthesis of the compounds described herein. The synthesis of the compounds of Formula (I), (II), I-11, I-12 and I-30 which are the subject of this invention may be accomplished by one or more of similar routes.

Example 1

Preparation of Compound i-11 from Starting Compound I-5b

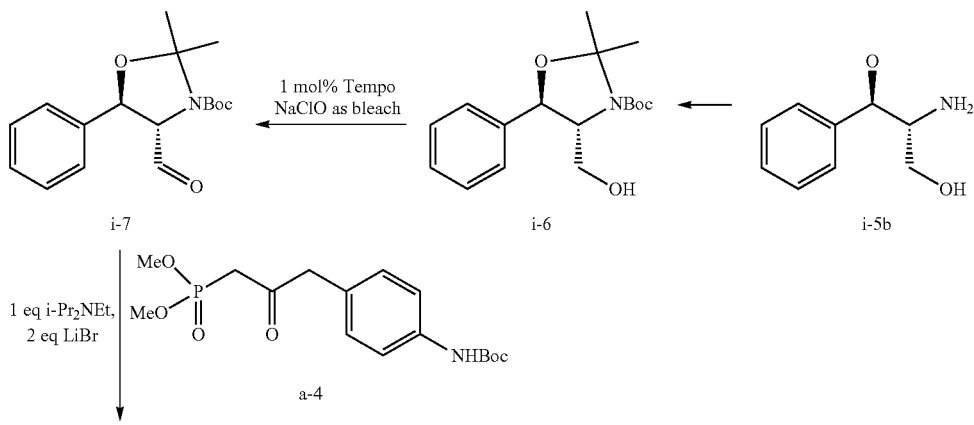

Scheme 1

-continued

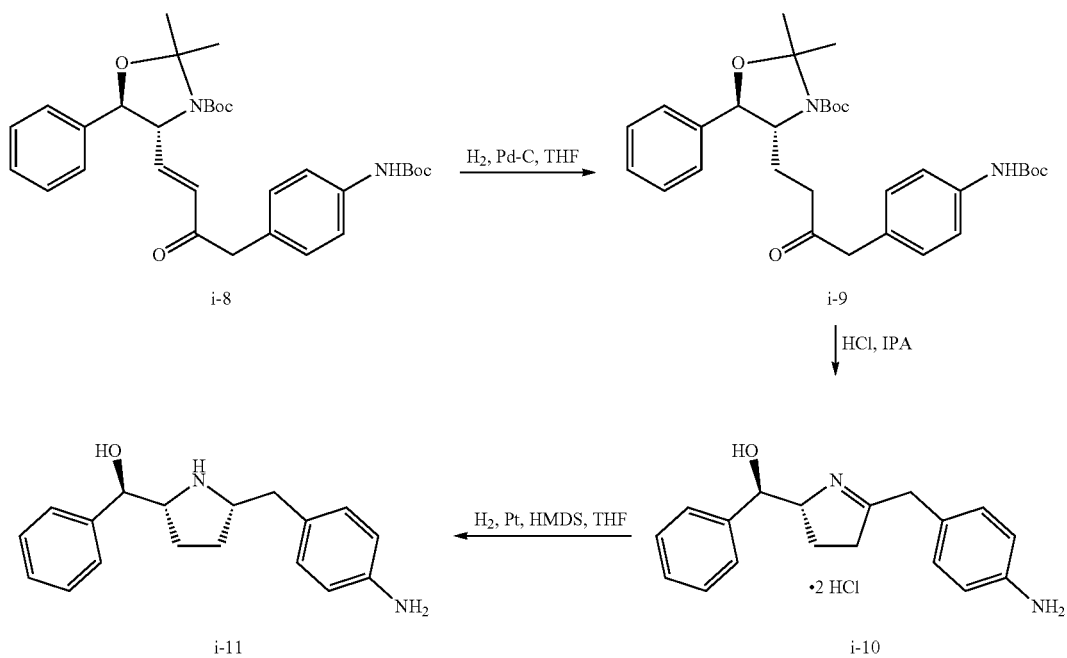

In Scheme 1, starting material compound I-5b was converted to compound i-6 by reacting with acetone and Boc$_2$O.

Once compound i-6 was obtained, it was converted to i-7 by TEMPO oxidation. For the TEMPO oxidation and subsequent HWE coupling step, a one-pot through process was used such that the crude steam of the aldehyde i-7 after phase cut was used directly for the HWE reaction to avoid solvent switch. Unsaturated ketone i-8 was isolated over 5 steps. Finally, compound i-8 was converted to compound i-11 through i-9 and i-10. Detailed experimental conditions are described below.

Step 1. Preparation of Acetonide-Boc Alcohol i-6 from I-5b

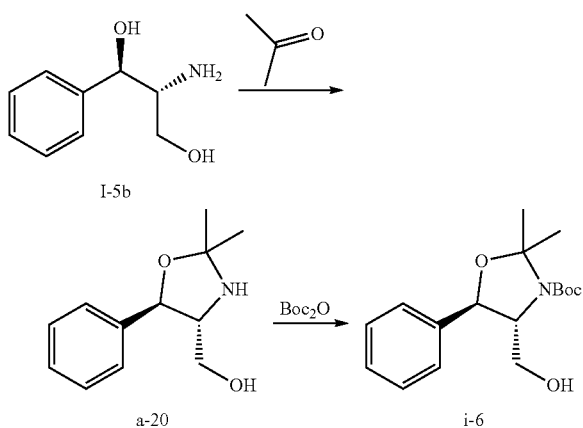

To a flask equipped a Dean-Stark trap was charged (1R,2R)-(−)-2-amino-1-phenyl-1,3-propanediol (I-5b) (10 g, 58.6 mmol), acetone (12.0 ml), and toluene (40.0 ml) (or MTBE). The slurry was heated to reflux for 22 h. To the solution was added di-tert-butyl dicarbonate (14.2 g, 64.5 mmol) at RT. The mixture was stirred at RT for 3.5 h, and to the mixture was added 1.5 g Boc$_2$O, then continued stirring overnight. The mixture was concentrated to 23.5 g oil, flushed with 40 mL heptane and concentrated to 23.7 g oil.

To the resulting mixture was added 18 mL heptane and the solution was seeded with 35 mg compound i-6. Crystalline seed bed initiated within 10 min. The resulting mixture was placed in −20° C. freezer overnight and then filtered and washed with 20 mL−20° C. heptane.

The wet cake was vacuum dried at 22° C. under N$_2$ overnight to afford 14.13 g compound i-6 as a beige solid (78.5%). Melting point (MP) was 69-72° C.

$^1$H NMR (CDCl$_3$) δ 7.45-7.30 (m, 5H), 4.80 (br s, 1H), 4.58 (br s, 1H), 3.82 (br m, 2H), 3.51 (br m, 1H), 1.70 (s, 3H), 1.60 (s, 3H), 1.52 (s, 9H); $^{13}$C NMR (CDCl$_3$) δ 154.5, 136.9, 129.2, 128.9, 127.6, 94.8, 81.7, 78.4, 67.9, 63.8, 28.5, 27.8, 26.1. Anal. Calcd. for C$_{17}$H$_{25}$NO$_4$: C, 66.43; H, 8.20; N, 4.56. Found: C, 66.33; H, 8.43; N, 4.59.

HPLC Method

Column: Waters Xbridge C18, 50 mm×4.6 mm, 2.5 m particle size;

Column Temp.: 25° C.; Flow rate: 1.0 mL/min; Detection: 210 nm & 254 nm;

Mobile phase: A: 1.0 mL of NH4OH (28% as NH3) dissolved in 1 L of water; B: MeCN Mobile Phase Program:

| | Time, min | | | | | | |
|---|---|---|---|---|---|---|---|
| | 0 | 4 | 8 | 12 | 16 | 16.5 | 20 |
| A % | 100 | 60 | 60 | 50 | 5 | 100 | 100 |
| B % | 0 | 40 | 40 | 50 | 95 | 0 | 0 |

Step 2. Preparation of Compound i-7 by TEMPO Oxidation of Compound i-6

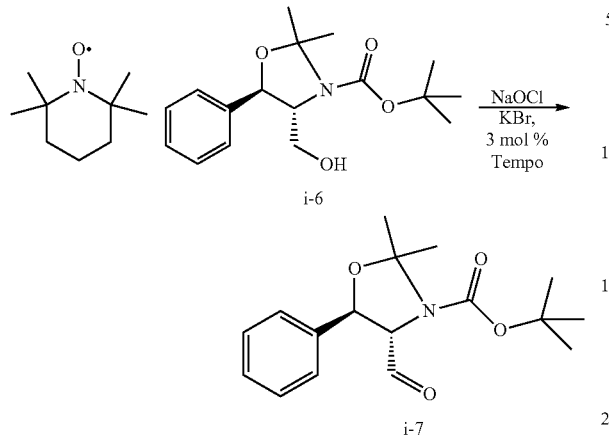

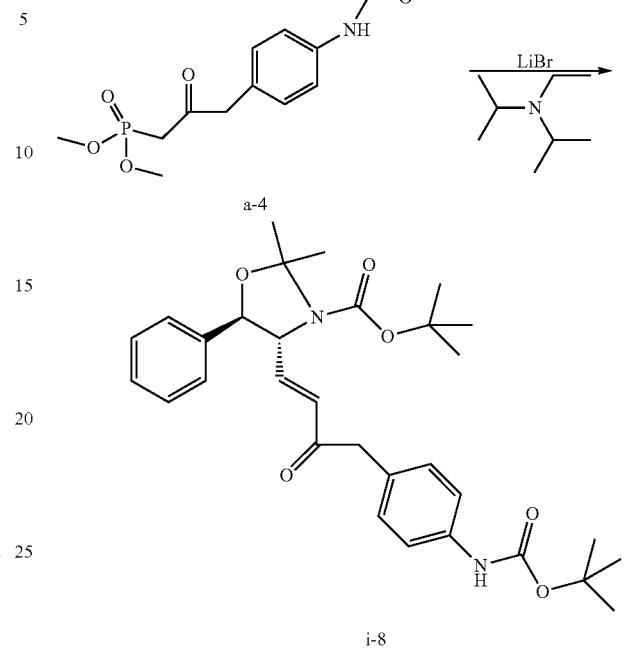

To a solution of i-6 alcohol in toluene (20 g assay, ~60 mL) was added acetonitrile (120 mL) at RT. KBr (1.16 g), NaHCO$_3$ (1.8 g) and water (40 mL) were then charged resulting in a biphasic mixture. The biphasic mixture was cooled to 5° C. and TEMPO (305 mg) was added. Then, NaClO solution (Clorox; 6 wt %; 101 g) was added dropwise at 0-5° C. over 2 h. After addition, the reaction was stirred at 5° C. for ~30 min. Conversion of >96% was obtained.

The reaction was quenched by dropwise addition of 10% sodium sulfite (50 mL) at 5° C. The organic layer was separated and directly used for the subsequent HWE coupling step without further purification. The assay yield was 17.5 g (88%) by $^1$H NMR using DMAc as internal standard.

Retention times of i-6 and i-7 using the following HPLC method were about 3.3 min and 3.9 min, respectively.
HPLC Method
Column: Zorbax, Eclipse Plus C18, 4.6×50 mm, 1.8 μm particle size;
Column Temperature: 22° C.; Flow Rate: 1.5 mL/min; UV Detection: 210 nm;
Mobile Phase: A: 95/5/0.1, H$_2$O/Methanol/H$_3$PO$_4$ B: 95/5, MeCN/methanol
Mobile Phase Program:

|   | Time, min | | |
|---|---|---|---|
|   | 0 | 5 | 6 |
| A % | 60 | 10 | 10 |
| B % | 40 | 90 | 90 |

Step 3. Preparation of i-8 by Horner Wadsworth Emmons (HWE) Coupling Reaction

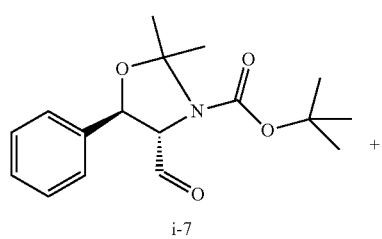

To a solution of i-7 aldehyde in wet toluene/acetonitrile (162 g solution; 17.5 g assay; 10.81 wt %) obtained above at −10° C. were added acetonitrile (140 mL), phosphonate a-4 (24.6 g) and LiBr (14.9 g) while the internal temperature was maintained below 0° C.

The reaction was warmed up to 0° C., and Hunig's base (22.2 g) was charged at 0-5° C. dropwise over 2 h. The resulting reaction mixture was stirred at 0-5° C. for 2-4 h and allowed to warm to RT, followed by aging at RT for 12 h. HPLC showed conversion (product/(product+aldehyde)) of >99%.

The slurry was cooled to 5° C., and a 10% aqueous solution of citric acid (~75 g) was added dropwise to adjust the pH to 6.5-7.0 while maintaining the batch temperature at 0-5° C. The aqueous phase was separated at 0-5° C. and discarded.

The organic layer was washed with saturated NaHCO$_3$ (57 mL) and with H$_2$O (57 mL) successively. The organic phase was solvent switched to IPA to a final volume of ~192 mL. The product was gradually crystallized during the distillation.

Water (16.4 mL, 0.6 vol.) was added, and the resulting slurry was heated to 49° C. to give a homogeneous solution. The resulting solution was cooled to 40° C. and seeded (0.27 g). The resulting mixture was aged at 40° C. for 2 h to establish a seed bed, and H$_2$O (93 mL) was charged dropwise at 40° C. over 3 h, followed by aging at 40° C. for 1 h. The slurry was allowed to cool to 5-10° C. over 2 h, followed by aging at 5-10° C. for 2 h.

The wet cake was washed with 50% H$_2$O/IPA (a 164 mL cold displacement wash followed by a 110 mL slurry wash). Suction dried under nitrogen gave the product as an off-white solid (24.9 g, 100 wt %, >99 LCAP, 80% isolated yield from aldehyde).

Using the following HPLC method, the retention times of i-7, a-4 and i-8 were about 3.0 min, 1.2 min and 3.8 min, respectively.

HPLC Method

Column: Zorbax, Eclipse Plus C18, 4.6×50 mm, 1.8 μm particle size

Column Temp: 40° C.; Flow Rate: 1.5 mL/min; UV Detection: 210 nm;

Mobile Phase: A: 0.1% $H_3PO_4$ B: MeCN

Mobile Phase Program:

|  | Time, min | | |
| --- | --- | --- | --- |
|  | 0 | 3 | 7 |
| A % | 60 | 10 | 10 |
| B % | 40 | 90 | 90 |

Step 4. Preparation of Compound i-9 from Compound i-8

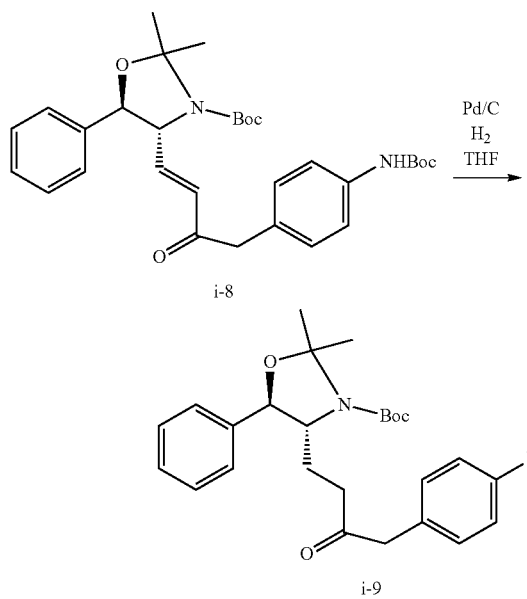

THF (84 g) followed by enone i-8 (19.07 g) and 10% Palladium on carbon (0.95 g) were charged to a hydrogenation vessel. The batch was hydrogenated for 90 min at 25° C. until uptake of hydrogen had ceased. The catalyst was removed through filtration of a bed of solka floc. The filtered residues were washed with THF (84 g). The combined organic phase was solvent switched to IPA to a final volume of 142 mL, which was directly used in the next step. Assay yield of 93% was obtained (17.8 g of i-9).

Using the following HPLC method, the retention times of i-8 and i-9 were about 11.2 min and 11.4 min, respectively.

HPLC Method

Column: HiChrom ACE C18 (250×4.6 mm), 3 μm particle size;

Column Temperature: 30° C.; Flow rate: 1.0 mL/min; Detection: 210 nm, 254 nm;

Mobile phase: A: 1 mL of phosphoric acid (85%) dissolved in 1 L of $H_2O$ B: MeCN Mobile Phase Program:

|  | Time, min | | | | | |
| --- | --- | --- | --- | --- | --- | --- |
|  | 0 | 5 | 8 | 15 | 16 | 20 |
| A % | 95 | 65 | 5 | 5 | 95 | 95 |
| B % | 5 | 35 | 95 | 95 | 5 | 5 |

Step 5. Preparing of Compound i-10 from Compound i-9

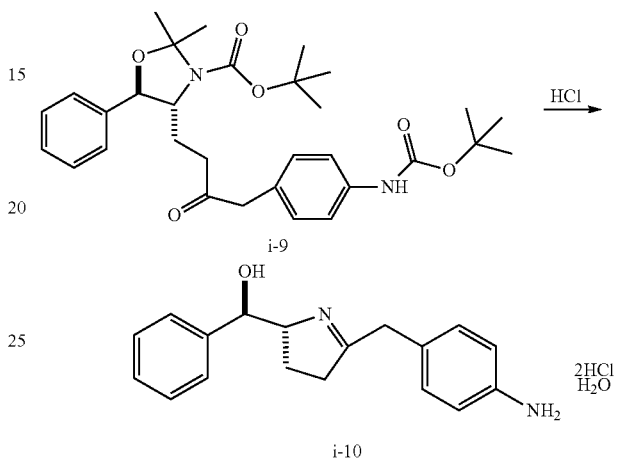

To a solution of the N-Boc-Ketone aniline i-9 (26.1 assay kg) in IPA (~125 g/L) was added 4N HCl in IPA (220.8 L) at RT. The reaction mixture was stirred vigorously at 20-25° C. for 24 h. The batch was distilled under reduced pressure, at constant volume by charging IPA up to one batch volume, to remove HCl. The batch was then concentrated to a final volume of ~215 L.

The resulting slurry was heated to 45° C., and IPAc (~430 L) was slowly added to the batch over 2-3 h. The slurry was then cooled to ~20° C. over 1-2 h and aged overnight. The batch was filtered, and the cake was washed with a 1:2 mixture of IPA:IPAc (52 L) followed by IPAc (52 L). The wet cake was dried at 45° C. under nitrogen atmosphere to give the cyclic imine bis-HCl monohydrate salt i-10 (16.1 kg). The isolated yield of 94% was obtained.

Using the same HPLC method as in Step 7 (i-8 to i-9), the retention times of i-9 and i-10 (bis-HCl salt) were about 11.3 min and 8.3 min, respectively.

Step 6. Preparation of Compound i-11 from Compound i-10

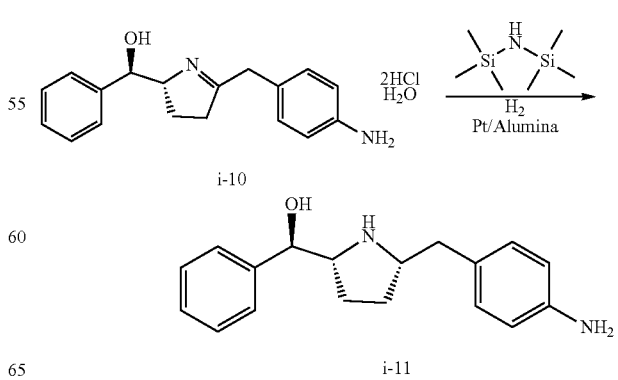

To a mixture of imine dihydrochloride monohydrate i-10 (12.0 g, 98.5 wt %) in THF (86 mL) under $N_2$ was added hexamethyldisilazane (10.95 g) while maintaining the batch temperature below 25° C. The resulting slurry was stirred vigorously at ambient temperature for 2 h.

A 300 mL autoclave was charged with a suspension of 5% platinum on alumina (0.605 g) in THF (32 mL), followed by the substrate slurry prepared above. The resulting mixture was stirred at RT under hydrogen (40 psig) until the hydrogen uptake ceased. The completion of the hydrogenation was confirmed by HPLC, and the vessel was inerted with nitrogen.

The reaction mixture was discharged, and the vessel rinsed with 96 mL of THF. The batch was filtered through a pad of Solka Floc, and the pad was rinsed with the THF vessel rinse (~96 mL). The combined filtrate was stirred with 0.5 M hydrochloric acid (129 mL) at ambient temperature for 1 h. The aqueous layer was separated. IPAc (39 mL) followed by 5 N sodium hydroxide (~15 mL) was added to adjust the pH to 10.0 with vigorous stirring.

The organic layer (~120 mL) was separated and treated with AquaGuard Powder (Meadwestvaco) (2.4 g) at RT for 2 h. The solution was filtered through a pad of Solka Floc, and the pad was rinsed with 2-propanol (18 mL). The combined filtrate was concentrated to 70 mL. The solution was distilled at the constant volume by feeding a total of 140 mL of 2-propanol, maintaining the batch temperature at 33-35° C. The resulting solution was concentrated to ~34 mL and heated to 50° C., followed by addition of $H_2O$ (6.3 mL). The resulting solution was cooled to 41-43° C. and seeded with pyrrolidine aniline hemihydrate (42 mg). The resulting mixture was aged at 41-43° C. for 1 h to establish a seed bed.

Water (60.9 mL) was charged at 41-43° C. over 6 h, and the resulting mixture was allowed to cool to 10° C. over 3 h, followed by aging at 10° C. for 2 h. The solids were collected by filtration and washed with 25% 2-propanol/$H_2O$ (50 mL). The wet cake was suction-dried at ambient temperature under nitrogen to afford 7.68 g of pyrrolidine aniline i-11 as hemihydrate.

$^1$H NMR (d$_6$-DMSO) δ 7.27 (m, 4H), 7.17 (m, 1H), 6.81 (d, J=8.1, 2H), 6.45 (d, J=8.1 Hz, 2H), 5.07 (s, br, 1H), 4.75 (s, 2H), 4.18 (d, J=7.0 Hz, 1H), 3.05 (m, 2H), 2.47 (dd, J=13.0, 6.7 Hz, 1H), 2.40 (dd, J=13.0, 6.6 Hz, 1H), 1.53 (m, 1H), 1.34 (m, 1 HO, 1.22 (m, 2H).

$^{13}$C NMR (d$_6$-DMSO) δ 146.5, 144.3, 129.2, 127.8, 127.4, 126.8, 126.7, 114.0, 76.8, 64.4, 60.1, 42.1, 30.2, 27.2.

Using the following HPLC method, the retention times of i-10 (bis-HCl salt) and i-11 were about 8.3 min and 8.5 min, respectively.

HPLC Method

Column: Waters Xbridge C18, 150×4.6 mm, 3.5 μm;

Column Temperature: 25° C.; Flow rate: 1 mL/min; Detection: 210 nm, 254 nm;

Mobile phase: A: Acetonitrile B: 0.1% aqueous NH4OH adjusted to pH9.5 with H

Mobile Phase Program:

| | Time, min | | | | |
|---|---|---|---|---|---|
| | 0 | 4 | 8 | 10 | 17 |
| A % | 99 | 65 | 65 | 30 | 30 |
| B % | 1 | 35 | 35 | 70 | 70 |

The crystalline anhydrous and hemihydrate forms of the pyrrolidine aniline compound i-11 were characterized by powder x-ray diffraction (PXPD) and shown in FIG. 1 and FIG. 2, respectively.

The crystalline anhydrous form of the pyrrolidine aniline compound i-11 was characterized by XRPD by the following reflections with the d-spacing and corresponding intensities listed below.

| Position [°2 Theta] | d-spacing [Å] | Relative Intensity [%] |
|---|---|---|
| 17.8453 | 4.97 | 100 |
| 25.1979 | 3.53 | 51.24 |
| 20.1002 | 4.42 | 39.04 |
| 23.9931 | 3.71 | 32.65 |
| 16.7073 | 5.31 | 27.98 |
| 25.5483 | 3.49 | 20.21 |
| 19.6576 | 4.52 | 20.2 |
| 13.8883 | 6.38 | 20.08 |
| 28.086 | 3.18 | 18.72 |
| 20.6498 | 4.30 | 16.23 |

The crystalline hemihydrate of the pyrrolidine aniline compound i-11 was characterized by XRPD by the following reflections with the d-spacing and corresponding intensities-listed below.

| Position [°2 Theta] | d-spacing [Å] | Relative Intensity [%] |
|---|---|---|
| 17.9681 | 4.94 | 100 |
| 17.8666 | 4.96 | 80.62 |
| 23.1905 | 3.84 | 73.82 |
| 15.3049 | 5.79 | 71.53 |
| 19.7955 | 4.49 | 65.46 |
| 19.9483 | 4.45 | 56 |
| 23.1076 | 3.85 | 54.38 |
| 25.3415 | 3.51 | 53.04 |
| 16.0859 | 5.51 | 44.07 |
| 25.6746 | 3.47 | 41.85 |

Example 2

Process for Making Compound i-12 from Compound i-14 and Compound i-15

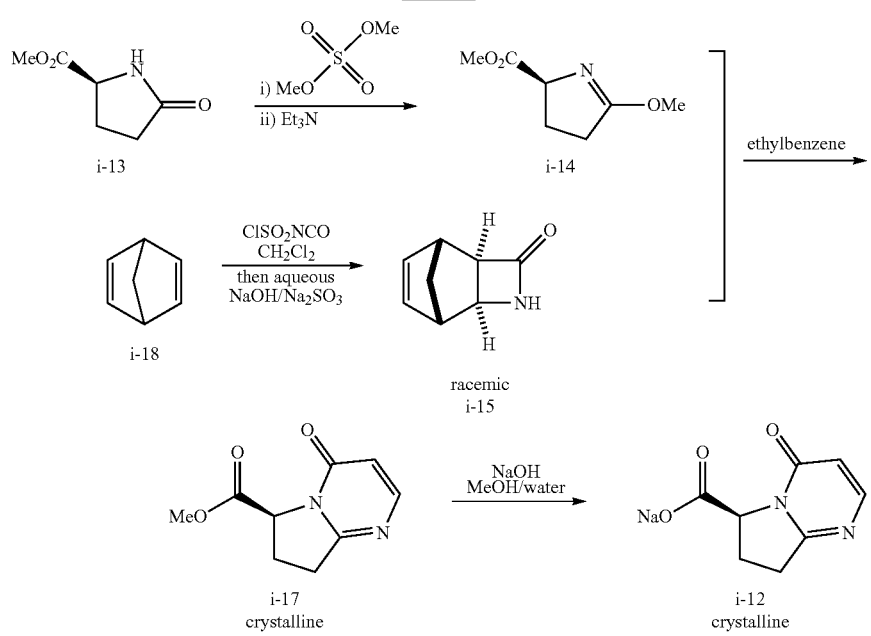

Step 1. Preparation of 3-Aza-tricyclo[4.2.1.0$^{2,5}$]non-7-en-4-one (beta-Lactam) i-15 from i-18

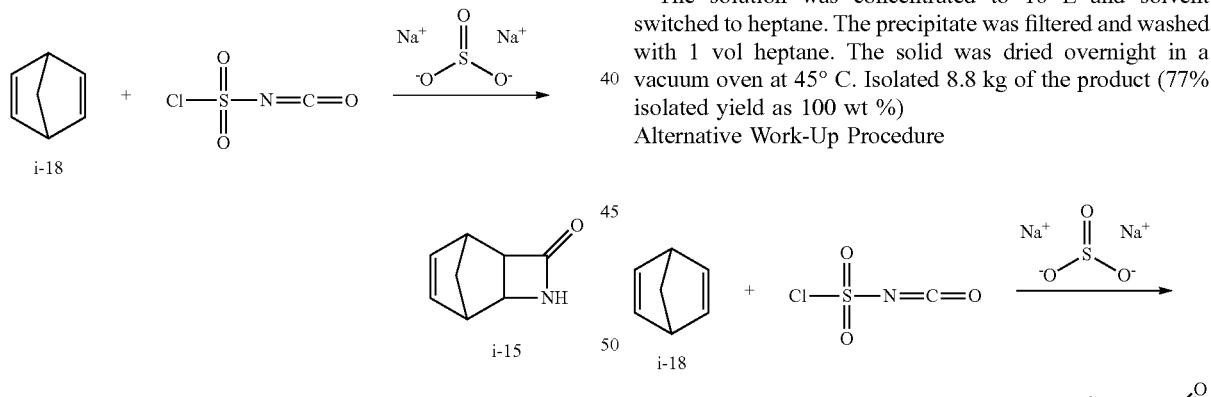

In a 100 L RBF fitted with an overhead stirrer, a thermocouple and a nitrogen inlet, was charged 36.8 L of DCM and 8.83 L of norbornadiene i-18. The solution was cooled to −15° C. A solution of 7.92 L of chlorosulfonylisocyanate in 11.2 L of DCM was added at a rate that keeps the internal temperature <5° C. The mixture was warmed to RT. After reaction was completed (by NMR), the reaction mixture was quenched into a 170 L cylinder vessel containing sodium sulfite (10.7 kg) in water (35.7 L) solution at a rate that keeps the internal temperature <15° C., maintaining a pH between 8.5 to 9.0 by addition of NaOH. Final pH was adjusted at 8.5.

Acetonitrile (24 L) was added and the layers were separated. If needed, 24 L of 20% brine solution was added to facilitate the viscous aqueous layer to flow. The top organic layer was separated and concentrated to 24 L and then filtered through an in-line filter into a 50 L RBF. At the prep area, removing residual inorganic salts via in-line filtration was problematic due to premature crystallization of the product. More acetonitrile and decanting at higher temperature were found helpful.

The solution was concentrated to 16 L and solvent switched to heptane. The precipitate was filtered and washed with 1 vol heptane. The solid was dried overnight in a vacuum oven at 45° C. Isolated 8.8 kg of the product (77% isolated yield as 100 wt %)

Alternative Work-Up Procedure

In a 1 L 3-neck RBF fitted with an addition funnel, a thermocouple, a magnetic stirrer, and a nitrogen inlet, was charged 184 mL DCM and 44.2 mL norbornadiene i-18. The solution was cooled to −12° C. A solution of 39.6 mL chlorosulfonylisocyanate in 56 mL DCM was added via the addition funnel at a rate that maintained a temperature range of −10 to 1° C. After the addition the mixture was allowed to warm to RT over 1-2 h. The reaction was monitored by $^1$H NMR showing the disappearance of the norbornadiene.

Work Up

In a 2 L 4-neck RBF fitted with a mechanical stirrer, an addition funnel and a pH probe, was charged 53.6 g sodium sulfite and 680 mL (17 vol) water. The reaction mixture was added via the addition funnel while simultaneously adding 10N NaOH keeping the temperature range −2 to 14° C. and pH >8.0. After the addition was complete the pH was adjusted to pH 8.5 and the mixture was allowed to warm to 15° C.

To the mixture was added 240 mL sec-BuOH. Organic layer was separated. The aqueous was back extracted 1× with 200 mL sec-BuOH.

Crystallization

In a 500 mL 3-neck RBF fitted with a distillation head temp probe and a mechanical stirrer, the combined organic solution was concentrated to 200 mL (5 vol) under vacuum with solution temperature kept at 25-27° C. (bath temp at 80° C.) bp=23° C. The solution was solvent switched to toluene till the ratio of toluene:BuOH=97:3 and the KF<200 ppm.

The slurry was cooled to 27° C. and to which was added 120 mL (3 vol) heptane dropwise via an addition funnel and aged overnight at room temperature.

The resulting mixture containing compound i-15 was filtered and washed with 1× w/40 mL (1 vol) heptane and dried in a vacuum oven at 40° C. overnight to yield compound i-15.

Step 2. Preparation of Compound i-14 from i-13

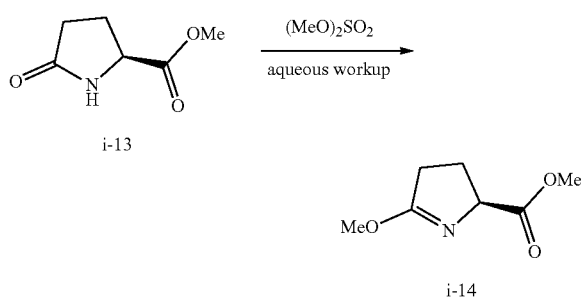

To a 20 L cylinder reactor equipped with an overhead stirrer, thermocouple, and nitrogen inlet was charged (S)-(+)-2-pyrrolidone-5-carboxylate i-13 (6.04 kg, 97 wt %), and dimethyl sulfate (5.33 L). The resulting reaction mixture was stirred at 53-58° C. for 12-15 h to afford product i-14 (>90 LCAP % conversion). The reaction mixture was cooled 25-30° C.

HPLC Method

Column: Zorbax Eclipse Plus C18 50×4.6 mm, 1.8 μm particle size;
Column Temp.: 25° C.; Flow Rate: 1.5 mL/min; Detection: 230 nm;
Mobile Phase: A: Water 0.1% $H_3PO_4$ B: Acetonitrile
Mobile Phase Program:

| Time, min | | |
|---|---|---|
| 0 | 5 | 6 |
| A % 90 | 5 | 5 |
| B % 10 | 95 | 95 |

To a 50 L room bottom reactor, equipped with an overhead stirrer, thermocouple, and nitrogen inlet, was charged triethylamine (8.93 L), and cooled to 10-15° C. The above reaction mixture was slowly added to TEA at 15-25° C. over 1 h, and stirred at RT for 0.5 h. The reaction mixture was transferred to a 100 L extractor, which contained toluene (40 L) and water (10 L).

After phase separation, the aqueous layer was extracted with toluene (1×20 L). The combined organic layers were washed with 10% $NaHCO_3$ (2×5 L) and brine (5 L). The organic layer was azotropically concentrated to afford an oil crude product methyl (2S)-5-methoxy-3,4-dihydro-2H-pyrrole-2-carboxylate (i-14) in toluene solution (expect KF<300 ppm, kg, 6.60 kg, 72.3 wt %, 74% yield after correction), which will be used in the next step.

Step 3. Preparation of Compound i-17 Through Cycloaddition/Retro Diels-Alder

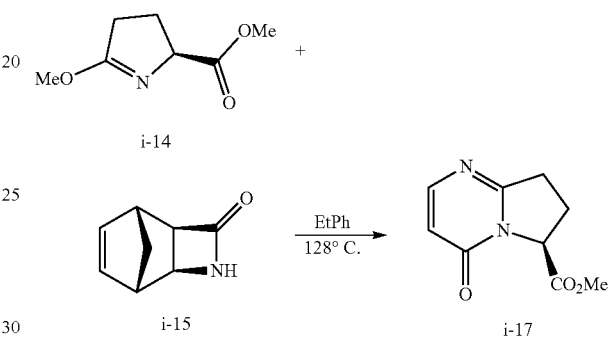

To a 50 L cylinder reactor, equipped with an overhead stirrer, thermocouple, nitrogen inlet, and Dean-Stark, was charged methyl (2S)-5-methoxy-3,4-dihydro-2H-pyrrole-2-carboxylate i-14 (6.60 kg, 72.3 wt %), beta-lactam i-15 (4.19 kg), and ethyl benzene (9.54 L). The resulting reaction mixture was stirred at 128° C. for 48 h. During the reaction, some low boiling point by-product such as methanol was removed through Dean-Stark in order to reach the interior temperature at 128° C. In prep lab, the internal temperature was 119-120° C., and the reaction was stirred at this temperature for 80 h (92% conversion by $^1$H NMR).

The reaction mixture was cooled to 35° C., diluted with toluene (14.3 L, 3 V) and Darco G-60 (1.43 kg) was added. The resulting mixture was stirred at the same temperature for 1 h. The Dacro G-60 was filtered off by passing through solka flock, washed with toluene (19.1 L). Assay product i-17 in the toluene solution was 3.81 kg (65%).

The combined filtrates were concentrated and purified by silica gel plug (22.5 kg silica gel, eluted by heptane 5 V; acetone/heptane=1:2, 15 V; acetone/heptane=2:1, 18 V).

The resulting product-rich solution was concentrated, and solvent-switched to EtOAc (6.5 L, total volume). Crystalline product i-17 was formed during solvent-switch to EtOAc. MTBE (7 L) was added slowly over 1 h (at this point, the ratio of EtOAc:MTBE was about 1:4 by $^1$H NMR). The resulting slurry was stirred at 5-10° C. for 1 h. The crystalline product i-17 was collected by filtration, washed with cold MTBE/EtOAc (5:1, 1 L), MTBE (3 L), dried under vacuum with nitrogen sweep to afford product i-17 (2.57 kg, >99 A % purity, 68% recovered yield, or 44% isolated yield from i-14). MP was 88 to 89° C.

The crystalline i-17 was important for the ee % upgrade, crystallization and isolation of product i-12 in the next step. Otherwise, the final step may require chiral separation or enzyme resolution.

HPLC Method

Column: Zorbax Eclipse Plus C18 50×4.6 mm, 1.8 μm particle size;

Column Temp.: 30° C.; Flow Rate: 1.5 mL/min; Detection: 230 nm;

Mobile Phases: A: Water 0.1% $H_3PO_4$ B: Acetonitrile

Mobile Phase Program:

|  | Time, min | | |
|---|---|---|---|
|  | 0 | 5 | 6 |
| A % | 90 | 5 | 5 |
| B % | 10 | 95 | 95 |

Step 4. Preparation of Compound i-12 Through Hydrolysis of Compound i-17

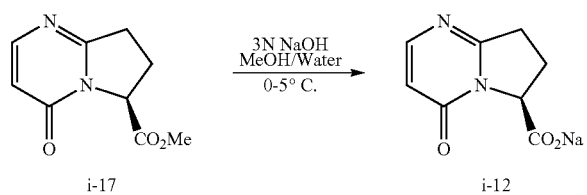

To a 50 L round-bottom, equipped with an overhead stirrer, thermocouple, nitrogen inlet, was charged methyl ester i-17 (4.70 kg), methanol (14.1 L), and water (9.4 L). The resulting homogenous solution was cooled to 0° C. 3 N sodium hydroxide (8.41 L) was slowly added through a pump at the rate 28 mL/min while maintaining the internal temperature at 0° C. to 5° C. After complete addition of the sodium hydroxide, the reaction mixture was stirred at 0° C. to 5° C. until the reaction was completed. The reaction mixture was adjusted to pH=6.5-7.0 with 5 N HCl.

The reaction mixture was concentrated and azotroped with toluene to a thick solution, and then solvent-switched to IPA. And the IPA solution was continued to azotrope to KF ≤6 wt % and adjusted to a total volume (14.1 L) with IPA. The resulting slurry was stirred at 0° C. to 5° C. for 1-2 h. A crystalline product i-12 as hydrate (3 equiv of water) was collected by filtration, washed with cold IPA (6 L), toluene (6 L), and dried under vacuum with nitrogen sweep overnight.

At this point, the crystalline hydrate product i-12 was continually dried in an oven at 50 0° C. to 55° C. under vacuum with flowing nitrogen for 50 h.

The crystalline compound of i-12 easily absorbs moisture in the air to form a hydrate. MP of the hydrate is 69.5 0° C. to 70.5° C.

HPLC Method

Column: Waters, AtlantisHPLC Silica 150×4.6 mm column, 3 μm particle size,

Column Temp.: 40° C. Flow rate: 1.00 mL/min; Detection: 210 nm;

Mobile Phase: A: Water 0.1% $H_3PO_4$ B: Acetonitrile

Mobile Phase Program:

|  | Time, min | | |
|---|---|---|---|
|  | 0 | 5 | 6 |
| A % | 90 | 5 | 5 |
| B % | 10 | 95 | 95 |

Example 3

Preparation of Compound of Formula (I) from Compound i-11 and Compound i-12

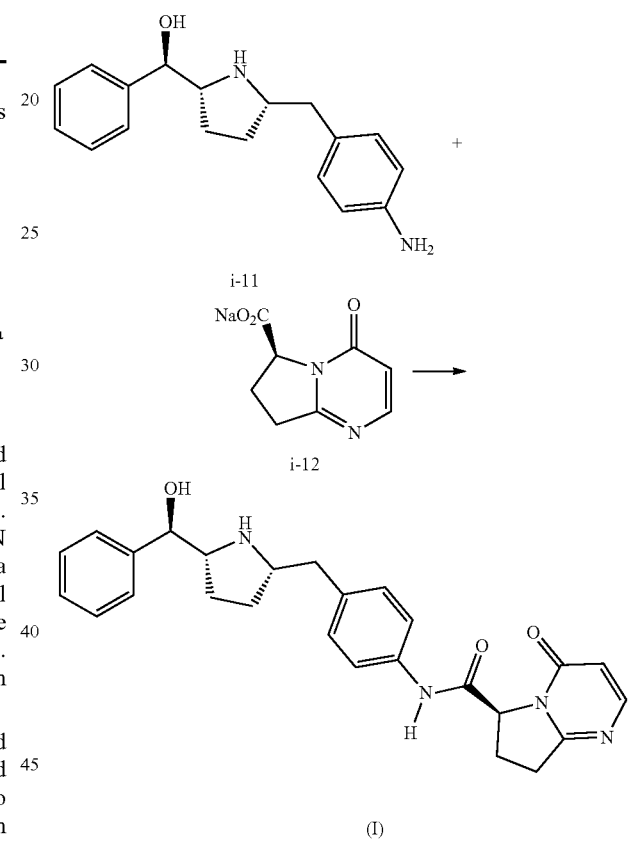

To a three neck flask equipped with a $N_2$ inlet, a thermo couple probe was charged pyrrolidine i-11 (10.0 g), sodium salt i-12 (7.87 g), followed by IPA (40 mL) and water (24 mL). 5 N HCl (14.9 mL) was then slowly added over a period of 20 min to adjust pH=3.3-3.5, maintaining the batch temperature below 35° C. Solid EDC hydrochloride (7.47 g) was charged in portions over 30 min. The reaction mixture was aged at RT for additional 0.5-1 h, aqueous ammonia (14%) was added dropwise to pH ~8.6. The batch was seeded and aged for additional 1 h to form a slurry bed. The rest aqueous ammonia (14%, 53.2 ml total) was added dropwise over 6 h. The resulting thick slurry was aged 2-3 h before filtration. The wet-cake was displacement washed with 30% IPA (30 mL), followed by 15% IPA (2×20 mL) and water (2×20 mL). The cake was suction dried under $N_2$ overnight to afford 14.3 g of compound of Formula (I).

$^1$H NMR (DMSO) δ 10.40 (s, NH), 7.92 (d, J=6.8, 1H), 7.50 (m, 2H), 7.32 (m, 2H), 7.29 (m, 2H), 7.21 (m, 1H), 7.16

(m, 2H), 6.24 (d, J=6.8, 1H), 5.13 (dd, J=9.6, 3.1, 1H), 5.08 (br s, OH), 4.22 (d, J=7.2, 1H), 3.19 (p, J=7.0, 1H), 3.16-3.01 (m, 3H), 2.65 (m, 1H), 2.59-2.49 (m, 2H), 2.45 (br s, NH), 2.16 (ddt, J=13.0, 9.6, 3.1, 1H), 1.58 (m, 1H), 1.39 (m, 1H), 1.31-1.24 (m, 2H).

$^{13}$C NMR (DMSO) δ 167.52, 165.85, 159.83, 154.56, 144.19, 136.48, 135.66, 129.16, 127.71, 126.78, 126.62, 119.07, 112.00, 76.71, 64.34, 61.05, 59.60, 42.22, 31.26, 30.12, 27.09, 23.82.

HPLC Method—For Monitoring Conversion

Column: XBridge C18 cm 15 cm×4.6 mm, 3.5 µm particle size;

Column Temp.: 35° C.; Flow rate: 1.5 mL/min; Detection: 220 nm;

Mobile phase: A. 5 mM $Na_2B_4O_7.10 H_2O$ B: Acetonitrile

Gradient:

| | Time, min | | | |
|---|---|---|---|---|
| | 0 | 6 | 8 | 10 |
| A % | 30 | 30 | 5 | 5 |
| B % | 70 | 70 | 95 | 95 |

HPLC Method—For Level of Amide Epimer Detection

Column: Chiralpak AD-H 5 m, 250 mm×4.6 mm.

Column Temp: 35° C.; Flow rate: 1.0 mL/min; Detection: 250 nm;

Mobile phase: Isocratic 30% Ethanol in hexanes+0.1% isobutylamine

Example 4

Preparation of Compound i-30 from Compound i-37

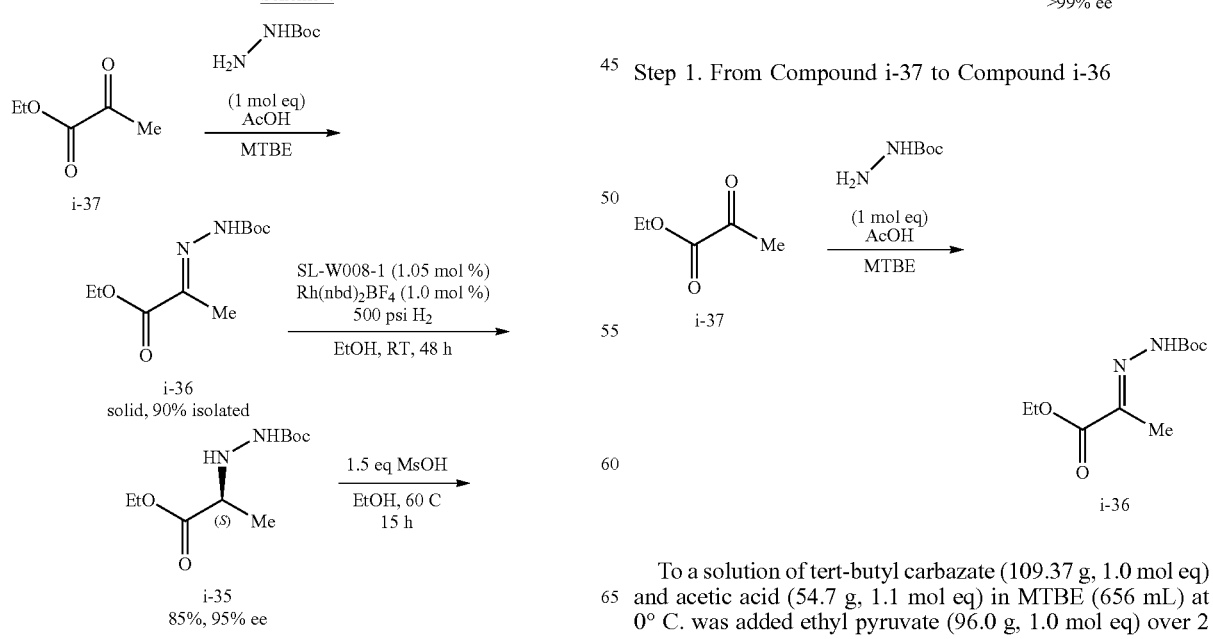

Step 1. From Compound i-37 to Compound i-36

To a solution of tert-butyl carbazate (109.37 g, 1.0 mol eq) and acetic acid (54.7 g, 1.1 mol eq) in MTBE (656 mL) at 0° C. was added ethyl pyruvate (96.0 g, 1.0 mol eq) over 2 h. The resulting slurry was aged at 0-5° C. for 3 h. The reaction was exothermic. The product began to crystallize out during the addition of ethyl pyruvate.

The resulting solids were collected by filtration, and the wet cake was washed with cold MTBE (220 mL displacement wash and 440 mL slurry wash) and suction-dried under $N_2$ to afford 172 g of the Boc-hydrazone compound i-36 as white solids. 90% Isolated yield. 8.6 g liquor losses (5%).

The concentration of i-36 in the supernatant prior to filtration was 18 mg/mL. The retention time of Boc-hydrazone using the following HPLC method was about 11.7 min.
HPLC Method—Achiral Method
Column: Phenomenex Luna C8 (250×4.6 mm I.D., 5 m);
Detector: UV 205 nm; Oven: 40° C.; Flow rate: 1.0 mL/min;
Injection vol: 10 μL;
Mobile phase A: 0.1% $H_3PO_4$ in Water (v/v); B: ACN
Gradient Program:

|  | Time, min | | | |
|---|---|---|---|---|
|  | 0 | 8 | 15 | 20 |
| A % | 95 | 40 | 5 | 5 |
| B % | 5 | 60 | 95 | 95 |

Step 2. From Compound i-36 to Compound i-35

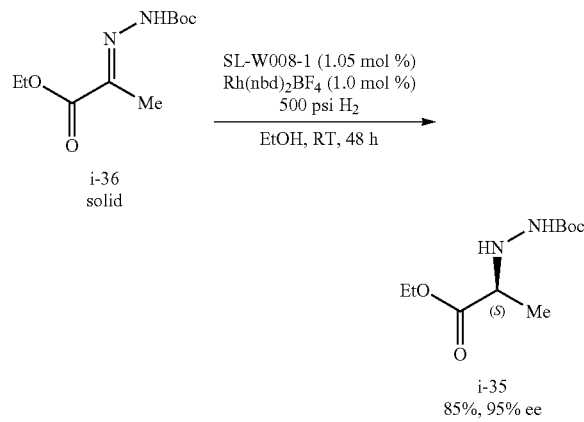

In a nitrogen-filled glovebox, $Rh(nbd)_2BF_4$ (374 mg, 1.00 mmol, 1.0 mol %) and SL-W008-1 (990 mg, 1.05 mol %) were weighed into a glass vial. Then 22 mL of degassed EtOH were added to give a homogeneous solution which was aged 16 h at 22° C. A slurry of 23.0 g (100 mmol) Boc-hydrazone i-36 in 100 mL of EtOH was prepared. This slurry was then charged to a 300 mL autoclave with a 20 mL EtOH flush. Degassed with vacuum/nitrogen purges, then charged the catalyst solution under nitrogen with a 10 mL EtOH flush. Hydrogenated at 500 psig $H_2$ for 48 h at 20-25° C. HPLC assay reveals 85% assay yield.

The batch was kept under nitrogen even after the reaction was complete. The product underwent oxidation to give the Boc-hydrazine in the presence of oxygen and rhodium. The target HPLC conversion is 96% (product/(product+starting material), at 210 nm), which corresponds to 99.3 mol % conversion.

Using the Achiral HPLC method described in Step 1, the retention times of i-35 and i-36 were about 11.5 min and 11.7 min, respectively.

Using the following Chiral HPLC method, the retention times of i-36, i-35 and the undesired hydrazide product were about 2.9 min, 3.8 min and 4.2 min, respectively.

Chiral Method
Chiralpak AD-RH, 2.5 mm×15 cm;
Mobile Phase: A=MeCN; B=0.1% (v/v) H3PO4 (aq)
1.0 mL/min; 1.0 uL injection, 35 C, 210 nm, 14 min runtime, 0.2 min post time
Gradient:

|  | Time, min | | | | | | |
|---|---|---|---|---|---|---|---|
|  | 0 | 1 | 7 | 8 | 10 | 10.2 | 14 |
| A % | 40 | 40 | 60 | 80 | 80 | 40 | 40 |
| B % | 60 | 60 | 40 | 20 | 20 | 60 | 60 |

Step 3. From Compound i-35 to Compound i-34

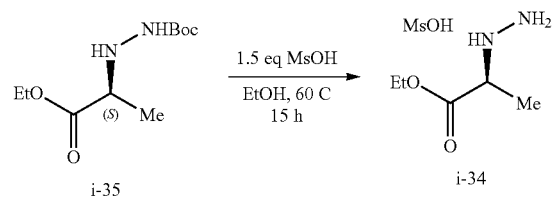

A solution of Boc-hydrazine i-35 (23.6 g assay, 1 mol eq) in EtOH (190 mL) was degassed by repeating an evacuation/$N_2$ refill cycle and treated with methanesulfonic acid (14.67 g, 1.5 mol eq) at 60° C. for 15 h until the consumption of the starting material (Boc-hydrazine) was confirmed by $^1H$ NMR. The resulting solution was concentrated to give the MSA salt of the deprotected hydrazine i-34 as an oil (34.51 g). The product was subjected to the subsequent cyclization step without further purification.

The targeted mol % conversion is 99% by $^1H$ NMR. The presence of oxygen can cause degradation of substrate/product. The reagents charges in the subsequent cyclization step were calculated by assuming 100% yield for this de-Boc step.

Step 4. From Compound i-34 to Compound i-32

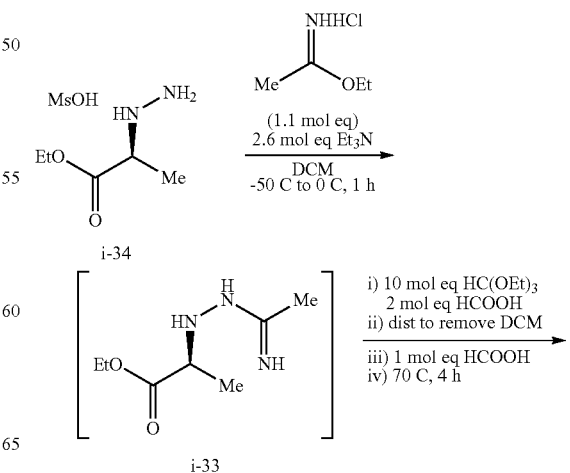

-continued

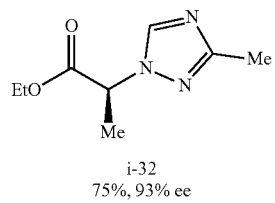

i-32
75%, 93% ee

A crude solution of the deprotected hydrazine i-34 (10.0 g as the free base) in EtOH was concentrated to ~38 mL (3.8 mL/g free base). The solution was distilled at the constant volume to remove EtOH while feeding toluene to give a biphasic solution.

The bottom layer contained the hydrazine MSA salt. The EtOH in the bottom layer was 0.7 mol eq (relative to the hydrazine) by $^1$H NMR.

The resulting biphasic solution was diluted with $CH_2Cl_2$ (100 mL) and cooled to −45° C., followed by addition of ethyl acetimidate HCl (10.29 g, 1.1 mol eq). N,N-diisopropylethylamine (27.39 g, 2.8 mol eq) was added dropwise over 1 h while maintaining the batch temperature between −45° C. and −40° C. The resulting suspension was allowed to warm to RT over 30 min and aged at RT for 2 h. The batch was cooled to −10° C., and triethyl orthoformate (51.2 g, 10 mol eq) and formic acid (4.14 g, 1.5 mol eq) were added dropwsie while maintaining the batch temperature below 0° C. The resulting mixture was distilled at 20-25° C. to collect 100 mL of solvents. Formic acid (4.14 g, 1.5 mol eq) was charged dropwise at RT, and the resulting mixture was heated to 70° C. for 4 h until the HPLC conversion reached 96 A % (i-32/(i-32+i-33)).

Formic acid with good quality (98%) was used. The enantiopurity of the product was eroded from 95% ee to 93% ee. Ee will be eroded further by prolonged aging. The racemization gets faster at higher temperatures. Reactions at lower temperature were sluggish and gave lower conversion.

The reaction was allowed to cool to 10° C. and diluted with $H_2O$ (25 mL), followed by aging at RT for 30 min to quench orthoformate. The pH of the mixture was adjusted to 8 with 15% $Na_2CO_3$ aq (~59.9 mL, 1.3 mol eq). The resulting mixture was extracted with EtOAc (70 mL×3). The combined organic layer was washed with 25% NaCl aq (70 mL) and 1 M phosphate buffer (pH 7, 70 mL). The solution was concentrated to ~104 mL, and the solvent was switched to 2-MeTHF by distillation while feeding a total of 440 mL 2-MeTHF. The resulting hazy solution was filtered to remove triethylamine HCl salt (~0.4 g). HPLC assay reveals 10.40 g of product (75% assay yield).

Quenching orthoformate was mildly exothermic and external cooling was required to maintain the batch temperature below 25° C. The spec for toluene level after solvent switch was 1.0 v/v %. Product losses in aqueous layers were typically <0.5% in the aqueous layer post back extractions and 2% in each brine and buffer wash. The buffer wash was helpful to promote the subsequent enzymatic resolution reaction.

Using the Achiral HPLC method described in Step 1, the retention times of i-33, i-32 and the ethyl formate by-product were about 4.0 min, 8.3 min and 8.4 min, respectively.

Step 5. From Compound i-32 to Compound i-30

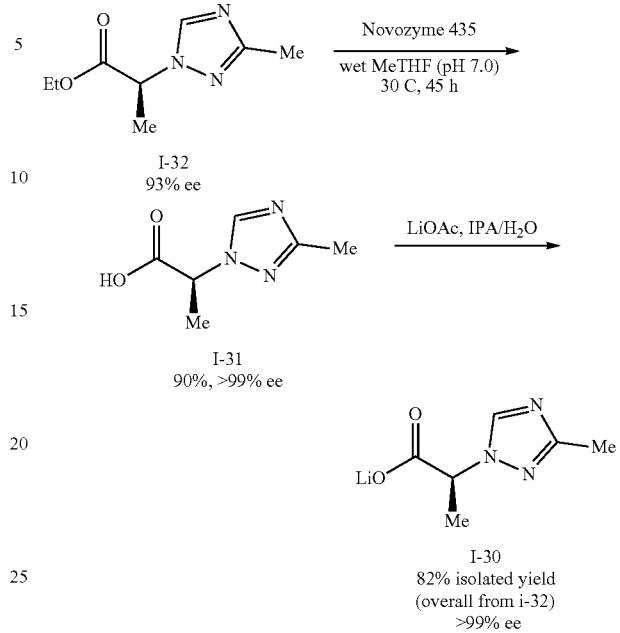

A crude solution of triazole ethyl ester i-32 (7.5 g assay, 93% ee) in 2-MeTHF was diluted with 250 mL of 2-Me-THF that was previously saturated with 1 M potassium phosphate buffer (pH 7.0). The resulting solution was heated to 30° C., followed by the addition of Novozyme 435 (15 g). The reaction was aged at 30° C. for 45 h.

The product ee was gradually decreased as the hydrolysis progressed. The reaction significantly slowed down as the desired enantiomer was consumed. If the ee of the starting material (triazole ester) is lower, the reaction has to be stopped at a lower conversion before the hydrolysis of the undesired enantiomer becomes competitive. The ee of the product was determined by SFC analysis. The conversion can be determined by RPLC.

The reaction mixture was filtered to remove the immobilized enzyme, and the enzyme was rinsed with 310 mL of buffer-saturated 2-Me-THF. The combined filtrate was assayed by HPLC. 5.74 g product (90% yield). >99% ee by SFC.

The solvent of the crude solution was switched from 2-Me-THF to IPA (total volume ~115 mL) by distillation. Lithium acetate (2.44 g) and $H_2O$ (9 mL) were added. The resulting slurry was aged at RT for 3 days and was azeotropically distilled while feeding a total of 230 mL of IPA (40° C., 50 Torr) to remove acetic acid. 0.6 v/v % $H_2O$ by KF. The slurry was cooled to RT and aged at RT for 4 h. The resulting solid was collected by filtration, washed with IPA and suction-dried to afford the triazole acid Li-salt i-30 as white solids (5.46 g). 92% isolated yield. >99.5% ee by SFC.

The enzyme can be recycled for re-use multiple times. The enzyme absorbs the triazole acid product and needs to be rinsed thoroughly after reaction to recover product. Adequate aging time for the Li-salt formation reaction was for from 12 hours to 3 days. The generating acetic acid needed to be distilled off to drive the Li-salt formation to completion. The addition of $H_2O$ was helpful to promote the Li-salt formation. LiOAc (weak base) was chosen in order to avoid the hydrolysis of the unreacted ester (low ee).

Using the Achiral HPLC method described in Step 1 (diluent: 5% MeCN/H₂O; product (i-30) peak gets broadened if prepared in different diluents), the retention times of i-30 and i-32 were about 5.7 min and 8.0 min, respectively.

Using the following Chiral HPLC method, the retention times of the desired enantiomer (S) and undesired enantiomer (R) were about 4.4 min and 7.1 min, respectively.
Chiral SFC Method (Triazole Acid and Li-Salt)
Column: IC SFC, 250×4.6 mm 5 μm
Detector: UV 210 nm; Temp.: 35 C; Flow rate: 3.0 mL/min (200 bar); Injection: 10 μL;
Mobile phase A: CO₂; B: 25 mM isobutylamine in MeOH
Gradient program: Isocratic, 10% B for 12 min Example 5

Preparation of Compound of Formula (II) from Compound i-11 and Compound i-30

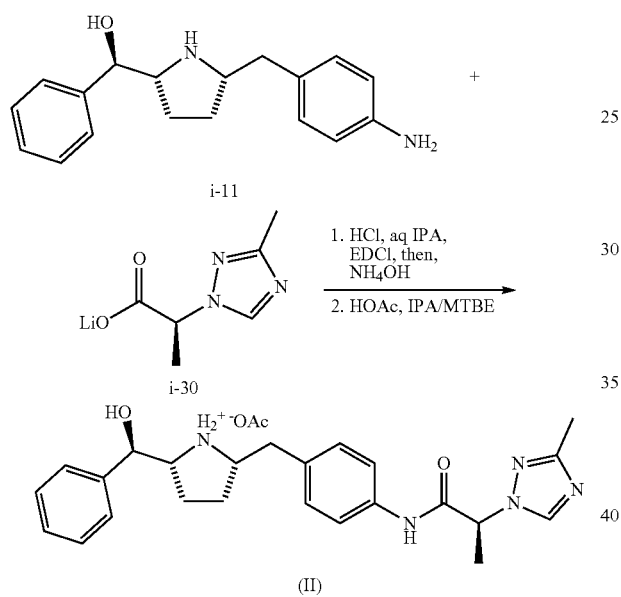

To a mixture of pyrrolidine i-11 (2.16 g) and lithium triazole salt i-30 (1.47 g) in water (11.6 mL) and IPA (6.48 mL) at 0-5° C. was added 5M HCl (3.52 mL) dropwise. The resulting solution was aged for additional 30 min. EDCI (1.76 g) was charged in portions over 1 h while the internal temperature was maintained 0-5° C. After 1-2 h age at 0-5 C, >98% conversion was obtained. The mixture was aged overnight at RT and diluted with EtOAc (20 mL) and pH adjusted to 7-8 with NH40H (14 wt %, ~4.5 mL) maintaining the internal temperature <5° C. The organic phase was separated and the aqueous phase was extracted with 10% IPA/EtOAc (10 mL).

The combined organic layer was washed with water (5 mL) and azetropically solvent switched to IPA to a final volume of 17 mL. MTBE (23 mL) was added. After 10% of 0.87 ml of HOAc was added at RT dropwise, the batch was seeded. The slurry was aged at RT for 1 h to form a good seed bed. The rest of HOAc was added dropwise at RT over 2 h. Then, the slurry was warmed to 40° C. and aged for 2 h before cooling to RT. After 2 h age at RT, the batch was filtered and washed with 30% IPA in MTBE (12 mL×2 displacement washes followed by a 12 mL slurry wash). The cake was vacuum oven dried at 40° C. to give 90% yield of compound of Formula (II) as an off-white solid.

Using the following HPLC method, the retention times of i-11 and Formula (II) were about 7.3 min and 8.4 min, respectively.
HPLC Method
Column: Restrek ultra II biphenyl, 4.6×1150 mm, 5.0 μm particle size;
Column Temp: 50° C.; Flow Rate: 1.5 mL/min; UV Detection: 220 nm;
Mobile Phase: A: 1% H₃PO₄ and 1% HClO₄; B: acetonitrile
Mobile Phase Program:

| | Time, min | | | | | |
|---|---|---|---|---|---|---|
| | 0 | 3 | 12 | 13 | 13.01 | 15 |
| A % | 95 | 95 | 85 | 5 | 95 | 95 |
| B % | 5 | 5 | 15 | 95 | 5 | 5 |

While the invention has been described and illustrated with reference to certain particular embodiments thereof, those skilled in the art will appreciate that various changes, modifications and substitutions can be made therein without departing from the spirit and scope of the invention. It is intended, therefore, that the invention be defined by the scope of the claims which follow and that such claims be interpreted as broadly as is reasonable.

What is claimed is:

1. A process of making a compound of formula (I-21):

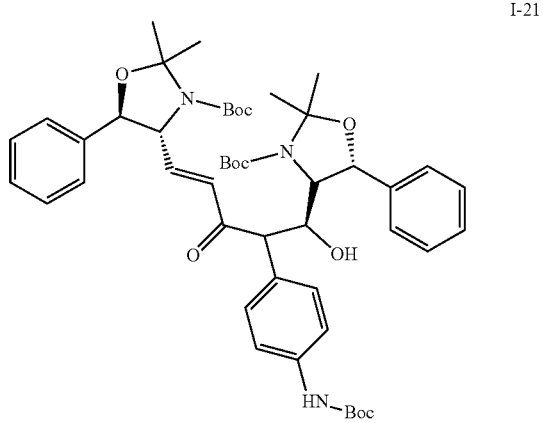

comprising reacting the compound of I-7:

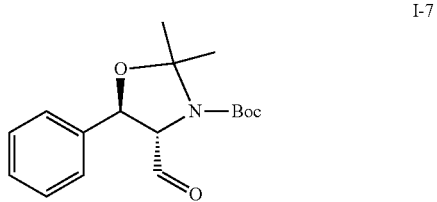 [SMILES: CC(C)(C)OC(=O)N1[C@H](C=O)[C@@H](c2ccccc2)OC1(C)C]

with a compound of formula A-4:

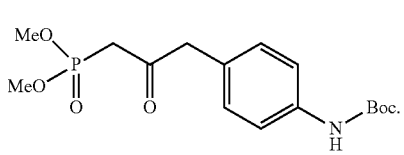

2. A method of increasing the yield of a compound of formula I-8:

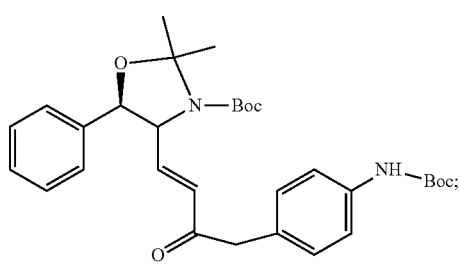

relative to the yield of a compound of formula (I-21):

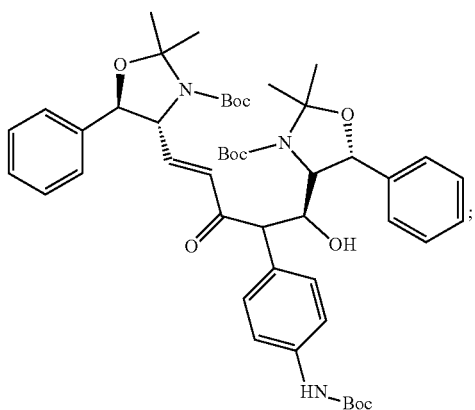

the method comprising adding a compound of formula I-7:

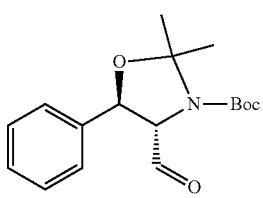

to a compound of formula A-4:

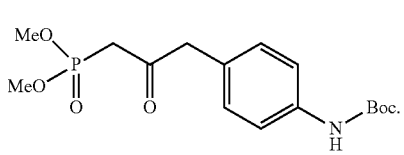

at a temperature of from about 25° C. to about 40° C.

3. The method of claim 2, further comprising adjusting the pH of the reaction mixture formed by the addition of I-7 to A-4 to a value of 6.5-7.0.

4. The method of claim 2, wherein the molar ratio of the compound of formula A-4 to the compound of formula I-7 is from about 1:1 to about 1.2:1.

5. The method of claim 2, further comprising dissolving the compound of formula A-4 in a solvent to form a solution prior to the addition of the compound of formula I-7.

6. The method of claim 5, wherein the solvent is selected from THF, MTBE, $CH_2Cl_2$, MeCN, toluene, and a mixture comprising two of the foregoing solvents.

7. The method of claim 5, further comprising adding a base to the solution prior to the addition of the compound of formula I-7.

8. The method of claim 7, wherein the base is a tertiary amine.

9. The method of claim 8, wherein the base is N,N-diisopropylethylamine.

10. The method of claim 7, further comprising adding a salt to the solution prior to the addition of the compound of formula I-7.

11. The method of claim 10, wherein the salt is a lithium halide.

12. The method of claim 11, wherein the salt is selected from lithium chloride and lithium bromide.

13. A compound which is:

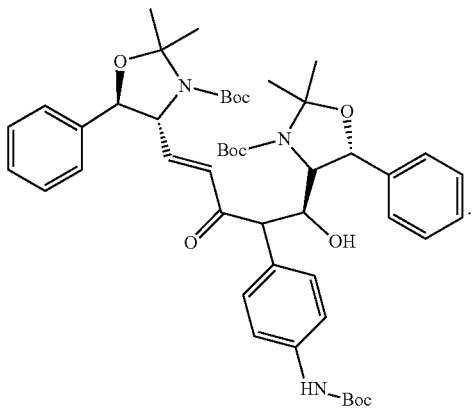

* * * * *